(12) United States Patent
Jerauld

(10) Patent No.: US 9,508,008 B2
(45) Date of Patent: *Nov. 29, 2016

(54) WEARABLE EMOTION DETECTION AND FEEDBACK SYSTEM

(71) Applicant: MICROSOFT TECHNOLOGY LICENSING, LLC, Redmond, WA (US)

(72) Inventor: Robert Jerauld, Kirkland, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/675,296

(22) Filed: Mar. 31, 2015

(65) Prior Publication Data

US 2015/0206011 A1 Jul. 23, 2015

Related U.S. Application Data

(63) Continuation of application No. 13/665,477, filed on Oct. 31, 2012, now Pat. No. 9,019,174.

(51) Int. Cl.
*G06K 9/00* (2006.01)
*A61B 5/11* (2006.01)
(Continued)

(52) U.S. Cl.
CPC ............ *G06K 9/00671* (2013.01); *A61B 5/11* (2013.01); *A61B 5/165* (2013.01); *A61B 5/486* (2013.01); *G02B 27/017* (2013.01); *G06K 9/00335* (2013.01); *G06T 11/60* (2013.01); *G10L 25/63* (2013.01); *G02B 2027/014* (2013.01);
(Continued)

(58) Field of Classification Search
CPC .................. G02B 27/01–27/0189; G02B 2027/01–2027/0198
USPC ........................................ 345/7–9
See application file for complete search history.

(56) References Cited

U.S. PATENT DOCUMENTS 6,417,969 B1 7/2002 DeLuca et al.
7,038,699 B2 5/2006 Sato et al.
(Continued)

FOREIGN PATENT DOCUMENTS

CA 2750287 A1 11/2011
GB WO 2011158010 A1 * 12/2011 ........... G09B 21/009
(Continued)

OTHER PUBLICATIONS

International Preliminary Report on Patentability dated May 6, 2015 in PCT Application No. PCT/US2013/067853.
(Continued)

*Primary Examiner* — Michael Pervan
(74) *Attorney, Agent, or Firm* — Daniel Choi; Micky Minhas

(57) ABSTRACT

A see-through, head mounted display and sensing devices cooperating with the display detect audible and visual behaviors of a subject in a field of view of the device. A processing device communicating with display and the sensors monitors audible and visual behaviors of the subject by receiving data from the sensors. Emotional states are computed based on the behaviors and feedback provided to the wearer indicating computed emotional states of the subject. During interactions, the device, recognizes emotional states in subjects by comparing detected sensor input against a database of human/primate gestures/expressions, posture, and speech. Feedback is provided to the wearer after interpretation of the sensor input.

18 Claims, 26 Drawing Sheets

(51) Int. Cl.
*A61B 5/16* (2006.01)
*G02B 27/01* (2006.01)
*A61B 5/00* (2006.01)
*G06T 11/60* (2006.01)
*G10L 25/63* (2013.01)
*G06F 3/01* (2006.01)

(52) U.S. Cl.
CPC .......... *G02B2027/0138* (2013.01); *G02B 2027/0178* (2013.01); *G06F 3/011* (2013.01)

(56) References Cited

U.S. PATENT DOCUMENTS

| | | |
|---|---|---|
| 7,124,425 B1 | 10/2006 | Anderson, Jr. et al. |
| 7,199,301 B2 | 4/2007 | Prittwitz |
| 7,308,112 B2 | 12/2007 | Fujimura et al. |
| 7,372,451 B2 | 5/2008 | Dempski |
| 7,587,747 B2 | 9/2009 | Maguire, Jr. |
| 7,632,187 B1 | 12/2009 | Farley et al. |
| 7,860,705 B2 | 12/2010 | Afify et al. |
| 8,188,880 B1 | 5/2012 | Chi et al. |
| 8,223,088 B1 | 7/2012 | Gomez et al. |
| 8,468,149 B1 | 6/2013 | Lung et al. |
| 2003/0133599 A1 | 7/2003 | Tian et al. |
| 2004/0210444 A1 | 10/2004 | Arenburg et al. |
| 2005/0038662 A1 | 2/2005 | Sarich et al. |
| 2005/0060365 A1 | 3/2005 | Robinson et al. |
| 2006/0009702 A1 | 1/2006 | Iwaki et al. |
| 2006/0105838 A1 | 5/2006 | Mullen |
| 2006/0149558 A1 | 7/2006 | Kahn et al. |
| 2006/0206310 A1 | 9/2006 | Ravikumar et al. |
| 2008/0002262 A1 | 1/2008 | Chirieleison |
| 2008/0055194 A1 | 3/2008 | Baudino et al. |
| 2008/0133336 A1 | 6/2008 | Altman et al. |
| 2008/0221862 A1 | 9/2008 | Guo et al. |
| 2008/0243473 A1 | 10/2008 | Boyd et al. |
| 2009/0048820 A1 | 2/2009 | Buccella |
| 2009/0293012 A1 | 11/2009 | Alter et al. |
| 2010/0079356 A1 | 4/2010 | Hoellwarth |
| 2010/0103196 A1 | 4/2010 | Kumar et al. |
| 2010/0153389 A1 | 6/2010 | Angell et al. |
| 2010/0238161 A1 | 9/2010 | Varga et al. |
| 2010/0318360 A1 | 12/2010 | Uehara |
| 2010/0328492 A1 | 12/2010 | Fedorovskaya et al. |
| 2011/0018903 A1 | 1/2011 | Lapstun et al. |
| 2011/0040155 A1 | 2/2011 | Guzak et al. |
| 2011/0161875 A1 | 6/2011 | Kankainen |
| 2011/0221656 A1 | 9/2011 | Haddick et al. |
| 2011/0310120 A1 | 12/2011 | Narayanan |
| 2012/0075168 A1 | 3/2012 | Osterhout et al. |
| 2012/0092328 A1 | 4/2012 | Flaks et al. |
| 2012/0143693 A1 | 6/2012 | Chung et al. |
| 2013/0038510 A1 | 2/2013 | Brin et al. |
| 2013/0044042 A1 | 2/2013 | Olsson et al. |
| 2013/0095460 A1 | 4/2013 | Bishop |
| 2013/0124185 A1 | 5/2013 | Sarr et al. |
| 2013/0293577 A1 | 11/2013 | Perez |
| 2014/0118225 A1 | 5/2014 | Jerauld |

FOREIGN PATENT DOCUMENTS

| | | |
|---|---|---|
| JP | H 10-123450 A | 5/1998 |
| WO | WO2012/158047 A1 | 11/2012 |

OTHER PUBLICATIONS

Response to Office Action filed May 18, 2015 in U.S. Appl. No. 13/464,945.

Final Office Action dated Jul. 7, 2015 in U.S. Appl. No. 13/464,945.

Poupyrev, et al., "Developing a Generic Augmented Reality Interface", In Proceedings of Computer, vol. 35 Issue 3, Mar. 2002, pp. 44-50.

Zhu, et al., "Personalized In-store E-Commerce with the PromoPad: An Augmented Reality Shopping Assistant", In Proceedings of Electronic Journal for E-commerce Tools and Applications, vol. 1 Issue 3, 2004, 19 pages.

Bajura, et al., "Merging Virtual Objects with the Real World: Seeing Ultrasound Imagery within the Patient", In Proceedings of 19th Annual Conference on Computer Graphics and Interactive Techniques, vol. 26 Issue 2, Jul. 1992, pp. 203-210.

Ajanki, et al., "Ubiquitous Contextual Information Access with Proactive Retrieval and Augmentation", In Proceedings of 4th International Workshop on Ubiquitous Virtual Reality, Mar. 8, 2010, 5 pages.

Katz, Leslie, "Tele Scouter Sends Translations Right to your Retina", Published on: Nov. 2, 2009, Available at: http://news.cnet.com/8301-17938_105-10388668-1.html?tag=mncol;txt.

Cowper, et al., "Improving Our View of the World: Police and Augmented Reality Technology", In Federal Bureau of Investigation, 2003, 68 pages.

Nilsson, et al., "Hands Free Interaction with Virtual Information in a Real Environment: Eye Gaze as an Interaction Tool in an Augmented Reality System", In Journal of PsychNology, vol. 7, Issue 2, 2009, pp. 175-196.

Van Krevelen et al., "A Survey of Augmented Reality Technologies, Applications and Limitations", The International Journal of Virtual Reality, vol. 9, Issue 2, Jun. 2010, pp. 1-20.

Kato, et al., "Marker Tracking and HMD Calibration for a Video-based Augmented Reality Conferencing System", In Proceedings of the 2nd IEEE and ACMInternational Workshop on Augmented Reality, Oct. 20-21, 1999, pp. 85-94.

Peternier, et al., "Chloe@University: An indoors, HMD-based Mobile Mixed Reality Guide", Retrieved on: Nov. 14, 2011, Available at: http://infoscience.epfl.ch/record/116211/files/Chloe_VRST07_FINAL.pdf.

"EON Coliseum", Retrieved on: Nov. 14, 2011, Available at: http://www.eonexperience.com/Coliseum.aspx.

Reitmayr, et al., "Collaborative Augmented Reality for Outdoor Navigation and Information Browsing", In Proceedings of the Symposium on Location Based Services and TeleCartography, 2004, 11 pages.

Fuhrman, et al., "Concept and Implementation of a Collaborative Workspace for Augmented Reality", In Vienna University of Technology, vol. 18, Issue 3, 1999, 11 pages.

U.S. Appl. No. 13/464,945, filed May 4, 2012.

International Search Report & The Written Opinion dated Jun. 18, 2014, International Application No. PCT/US2013-067853.

Amendment dated Oct. 8, 2014, in U.S. Appl. No. 13/464,945, filed May 4, 2012.

Office Action dated Oct. 22, 2014, in U.S. Appl. No. 13/464,945, filed May 4, 2012.

Office Action dated May 8, 2014, in U.S. Appl. No. 13/464,945, filed May 4, 2012.

International Search Report & The Written Opinion dated Aug. 1, 2013, International Application No. PCT/US2013/039431.

English Abstract of Japanese Publication No. JPH10-123450 published on May 15, 1998.

Lee, et al., "Combining Context-Awareness with Wearable Computing for Emotion-based Contents Service", In Proceedings of International Journal of Advanced Science and Technology, vol. 22, Sep. 2010, pp. 12.

Mura, Gökhan, "Wearable Technologies for Emotion Communication", Retrieved on: Jun. 26, 2012, Available at: http://jfa.arch.metu.edu.tr/archive/0258-5316/2008/cilt25/sayi_1/153-161.pdf.

Harrison, et al., "Using Multi-modal Sensing for Human Activity Modeling in the RealWorld", Retrieved on: Jun. 26, 2012, Available at: http://cs.gmu.edu/jpsousa/classes/895/readings/0463.pdf.

Ball, et al., "Emotion and Personality in a Conversational Character", Retrieved on: Jun. 26, 2012, Available at: http://research.microsoft.com/pubs/68709/wecc-98.doc.

"Meeting Georgios Papastefanou at the WT conference 2012", Retrieved on: Jun. 26, 2012, Available at: http://www.wearable-technologies.com/meeting-georgios-papastefanou-at-the-wtconference-2012.

(56) References Cited

OTHER PUBLICATIONS

Notice of Allowance and Fees Due in U.S. Appl. No. 13/665,477 mailed Dec. 31, 2014.
Amendment in U.S. Appl. No. 13/665,477 mailed Sep. 9, 2014.
Non-Final Rejection in U.S. Appl. No. 13/665,477 mailed May 9, 2014.
Amendment dated Jan. 15, 2015, in U.S. Appl. No. 13/464,945, filed May 4, 2012.
Office Action dated Feb. 17, 2015, in U.S. Appl. No. 13/464,945, filed May 4, 2012.
Response to Office Action filed Sep. 23, 2015 in U.S. Appl. No. 13/464,945.
Office Action dated Oct. 6, 2015 in U.S. Appl. No. 13/464,945.
Response to Office Action filed Jan. 6, 2016 in U.S. Appl. No. 13/464,945, 10 pages.
Final Office Action dated Mar. 22, 2016 in U.S. Appl. No. 13/464,945.

* cited by examiner

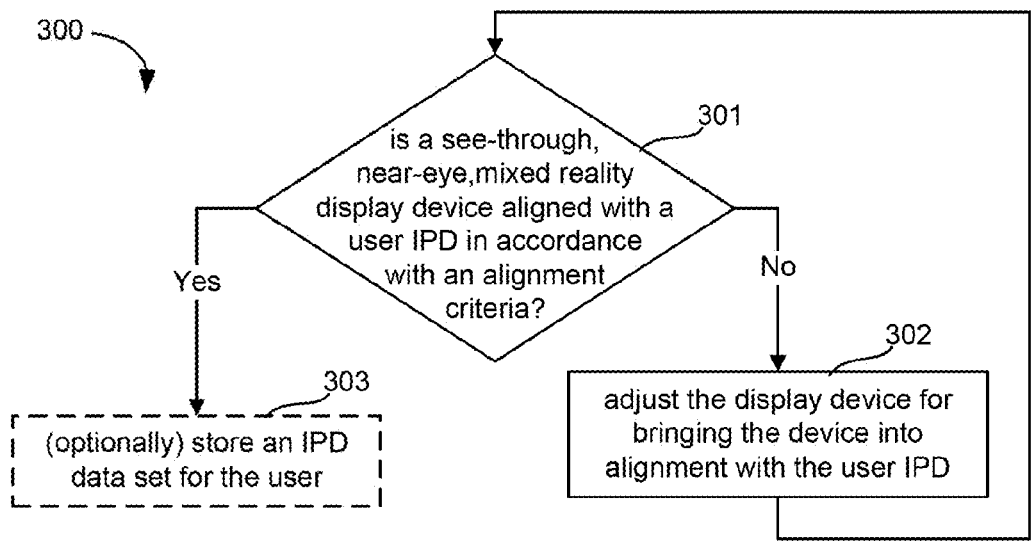
FIG. 3A
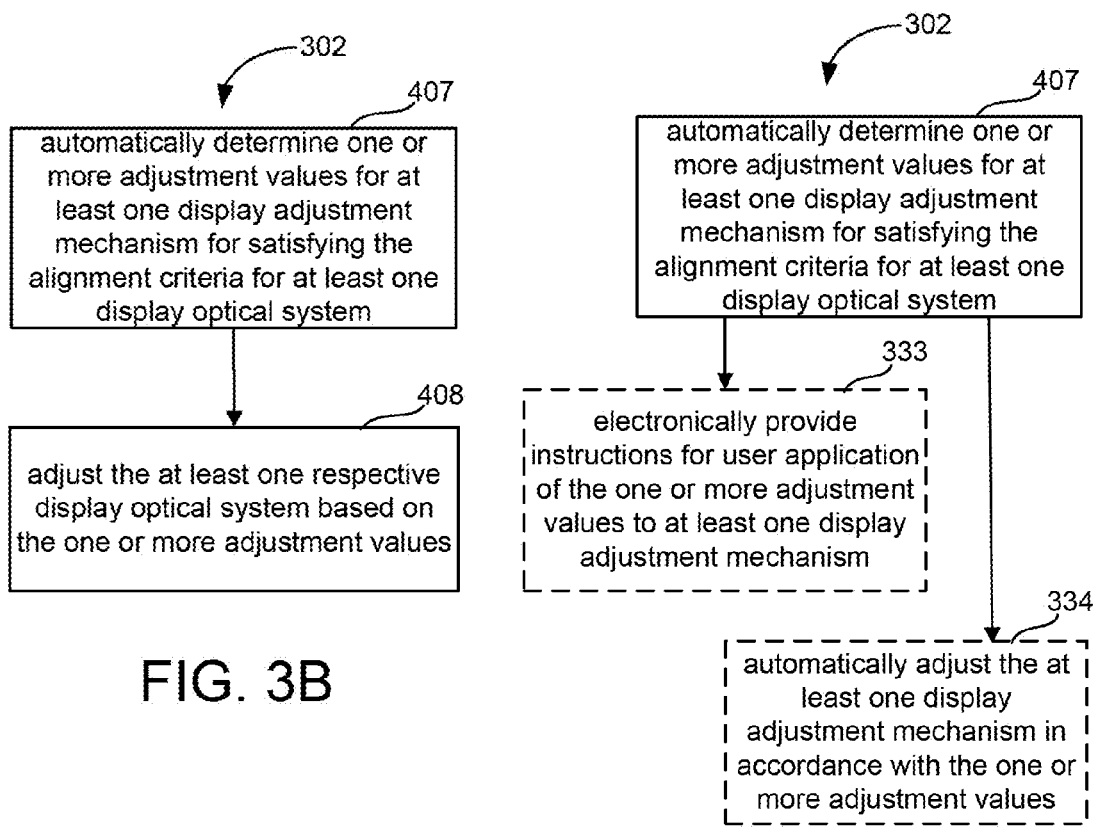
FIG. 3B
FIG. 3C

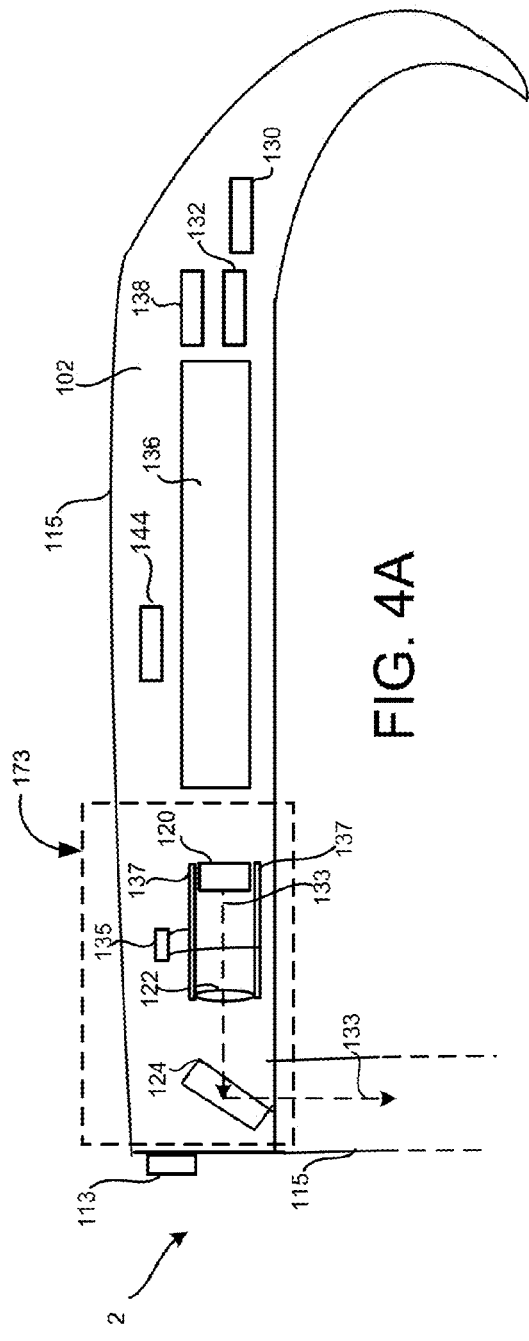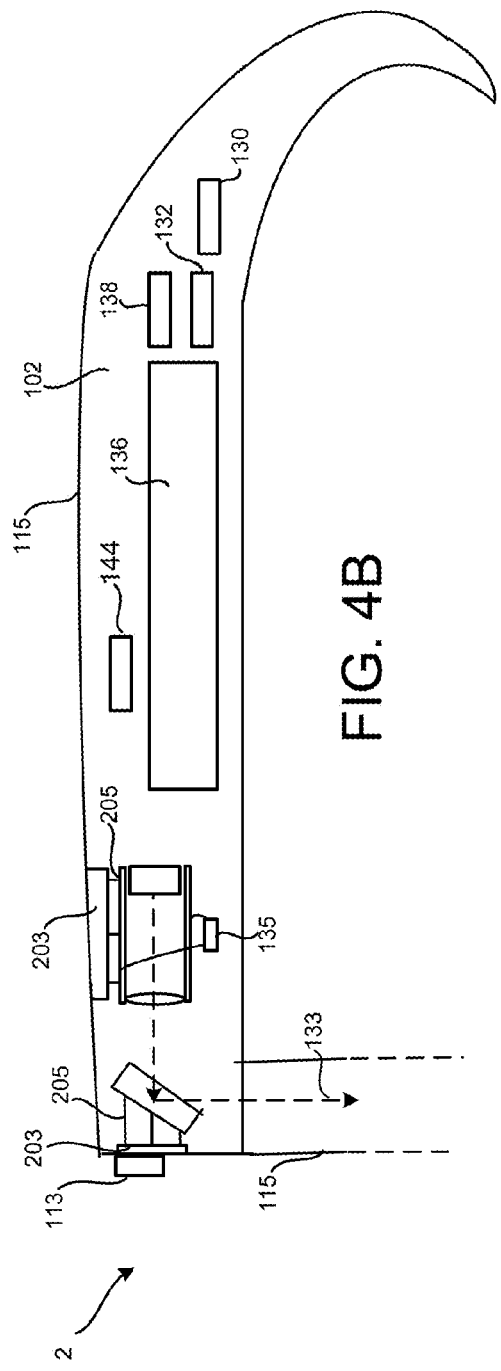

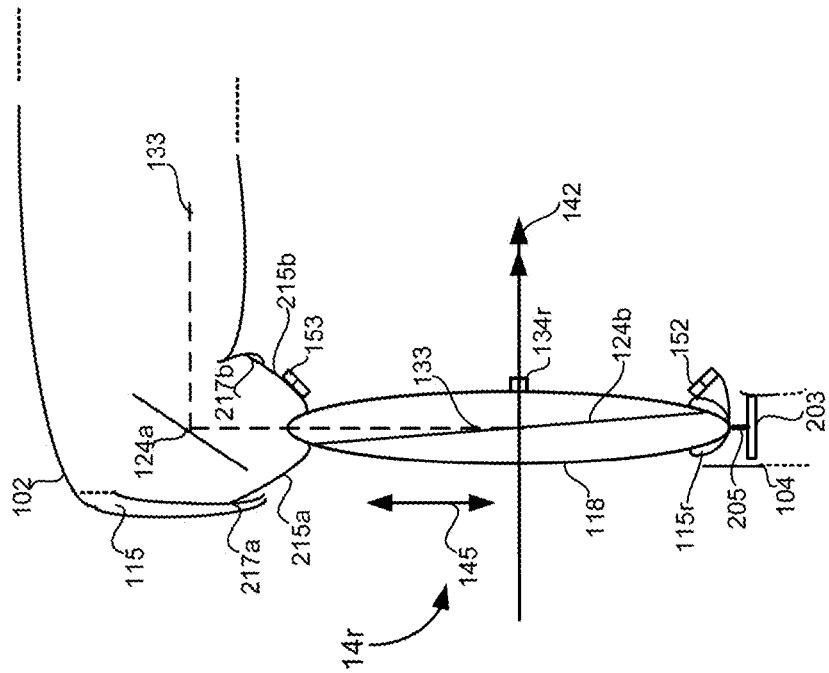
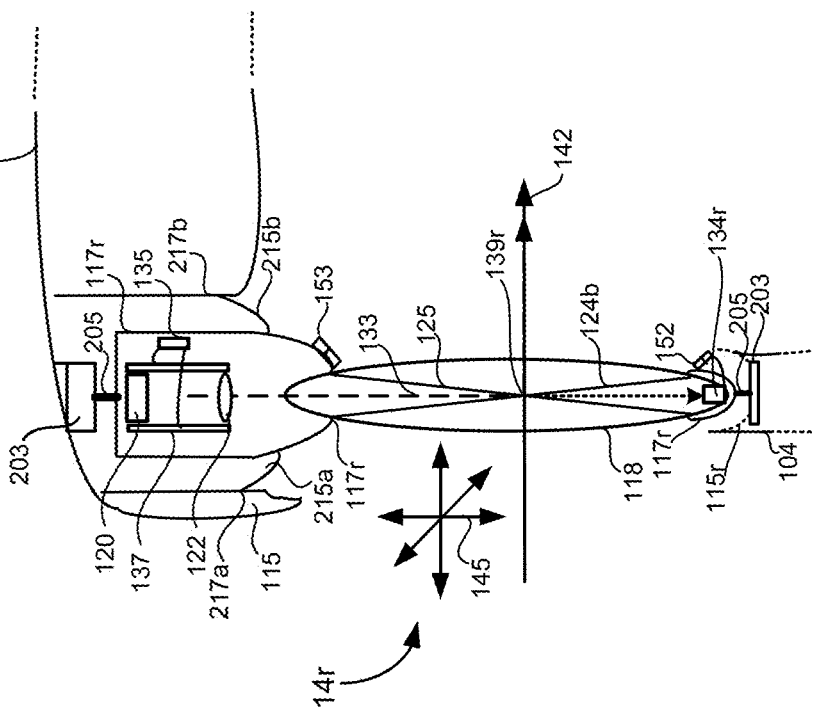

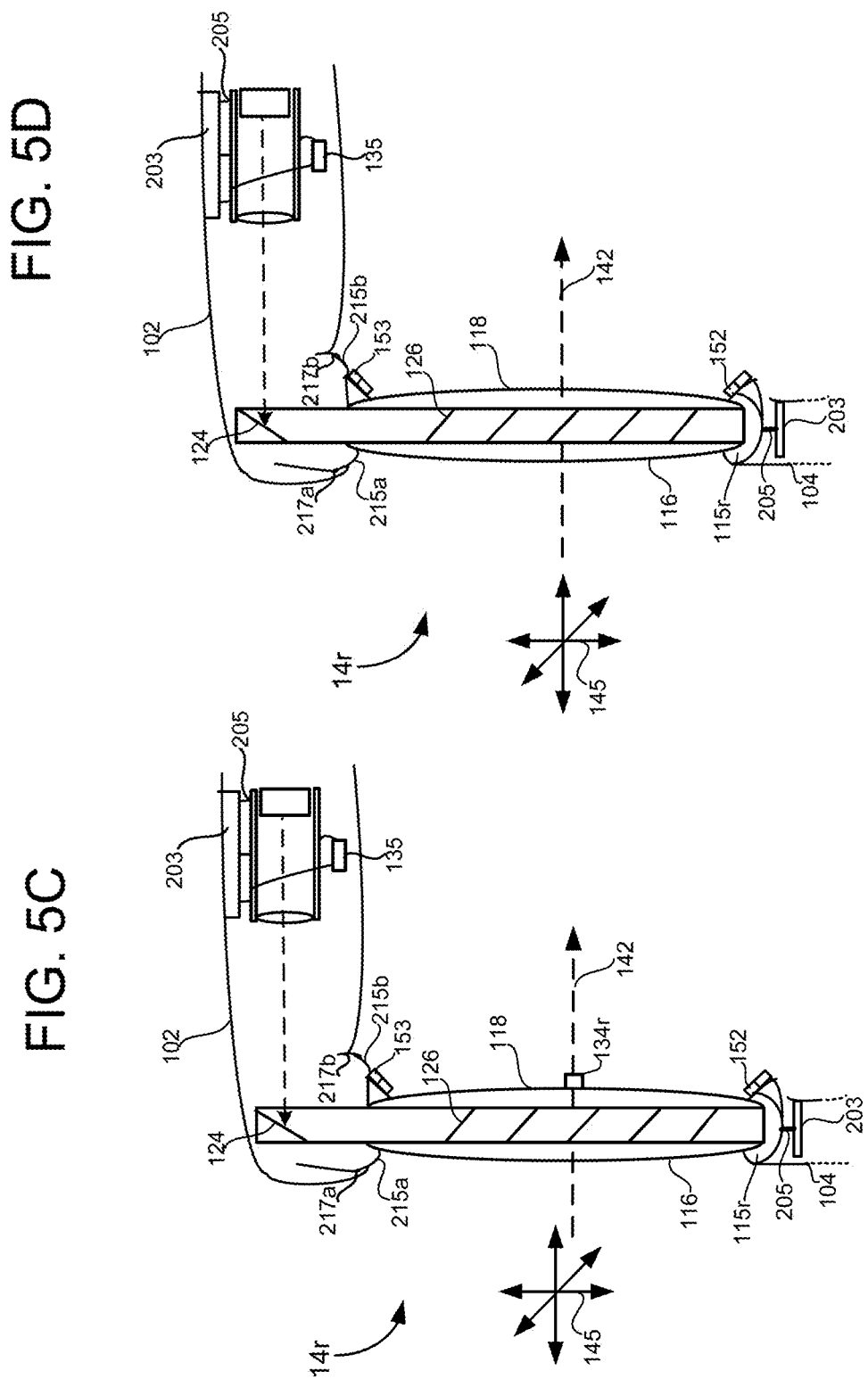

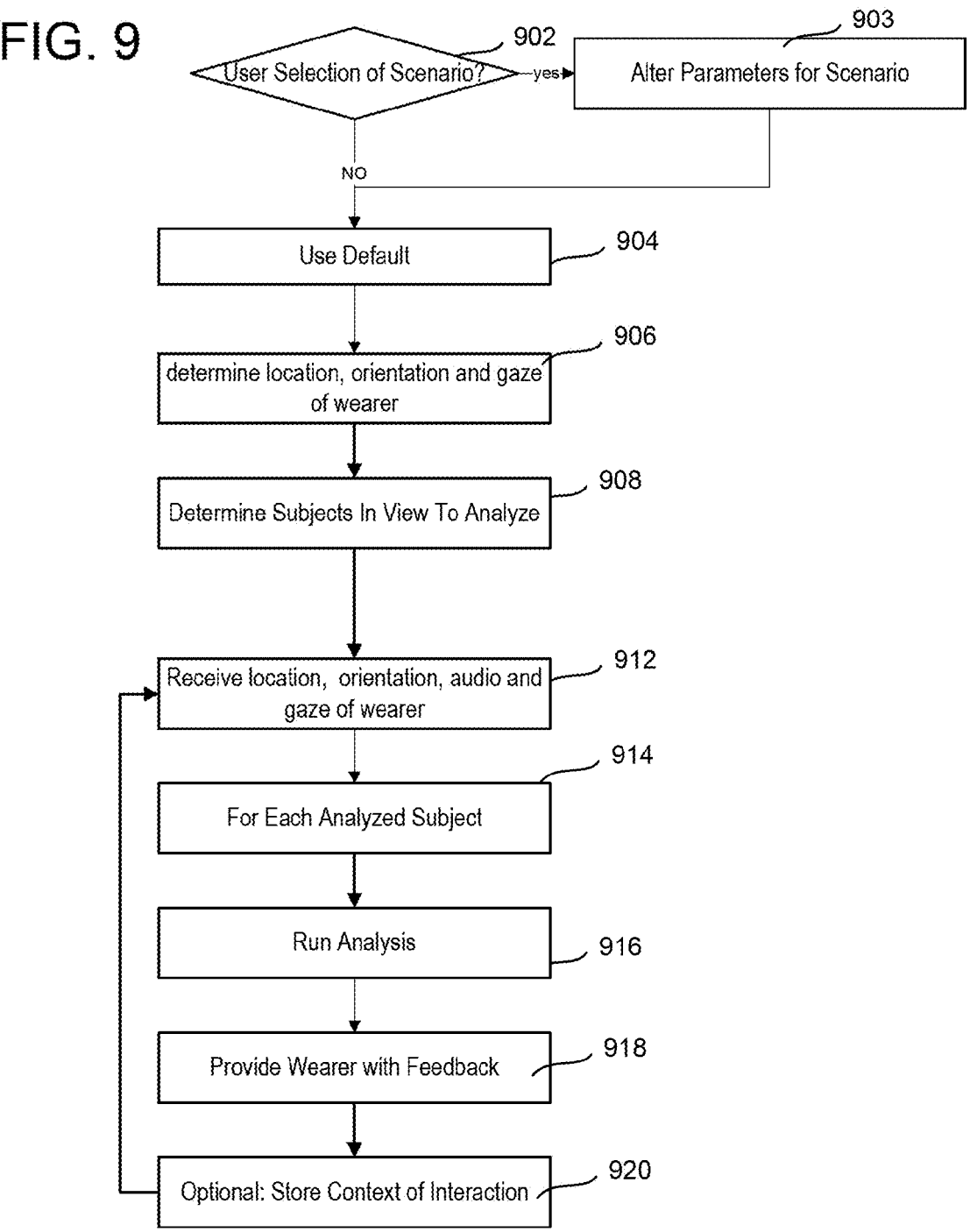

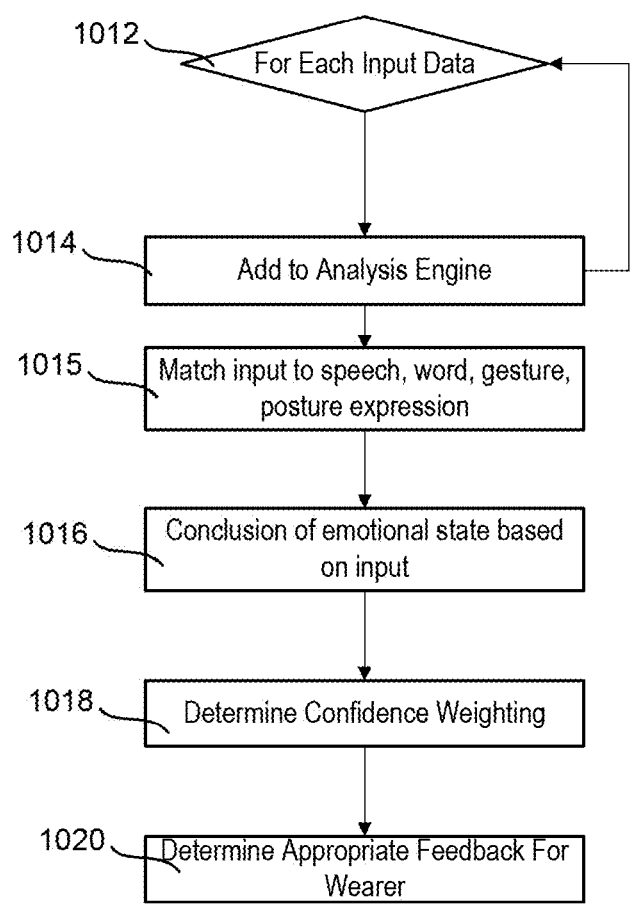

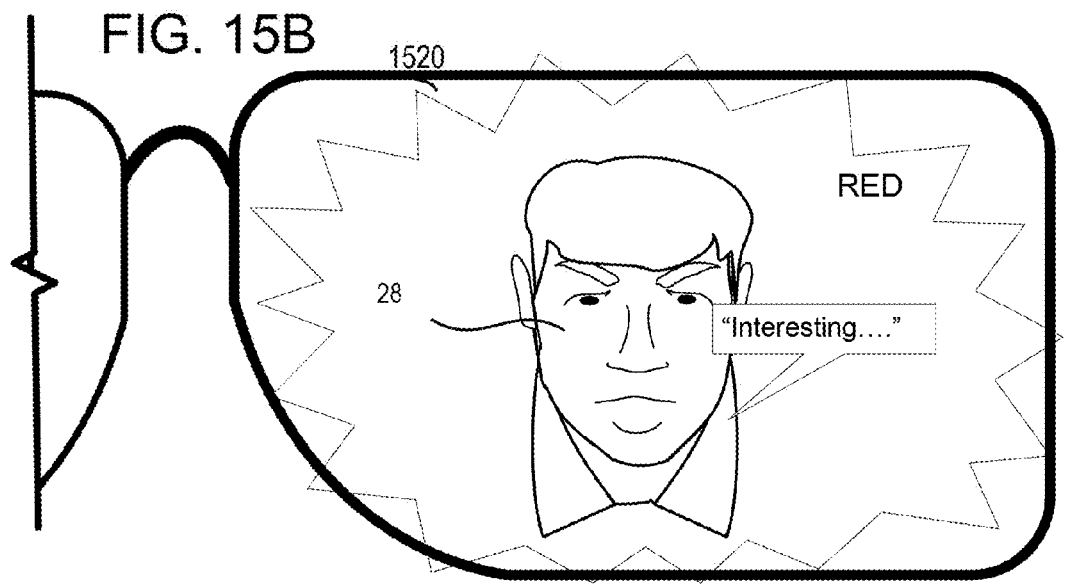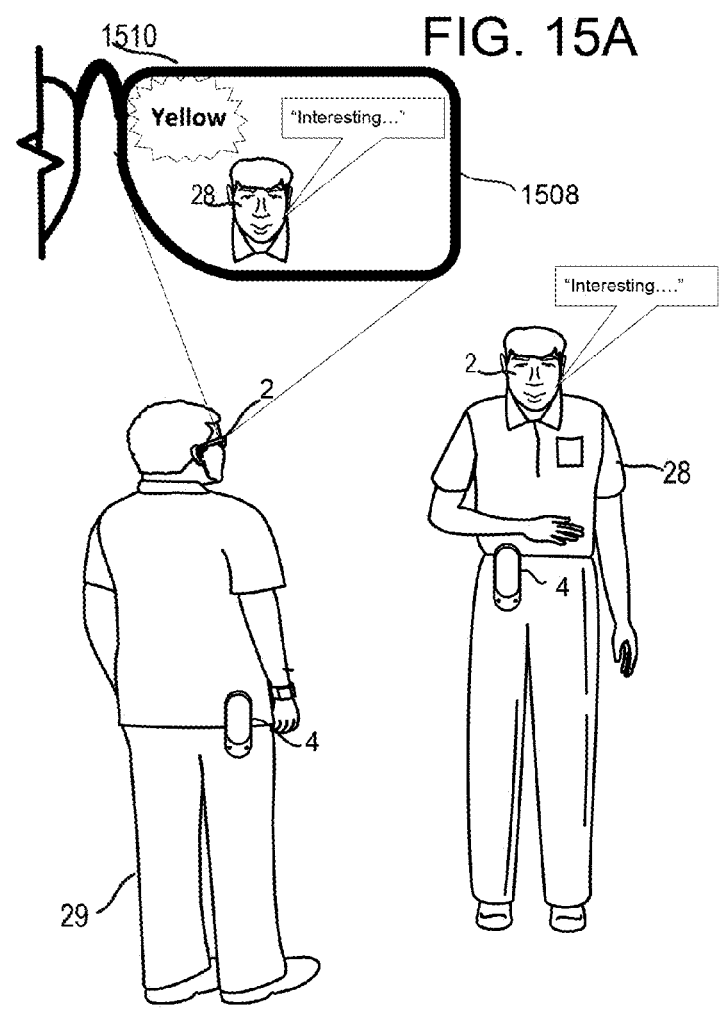

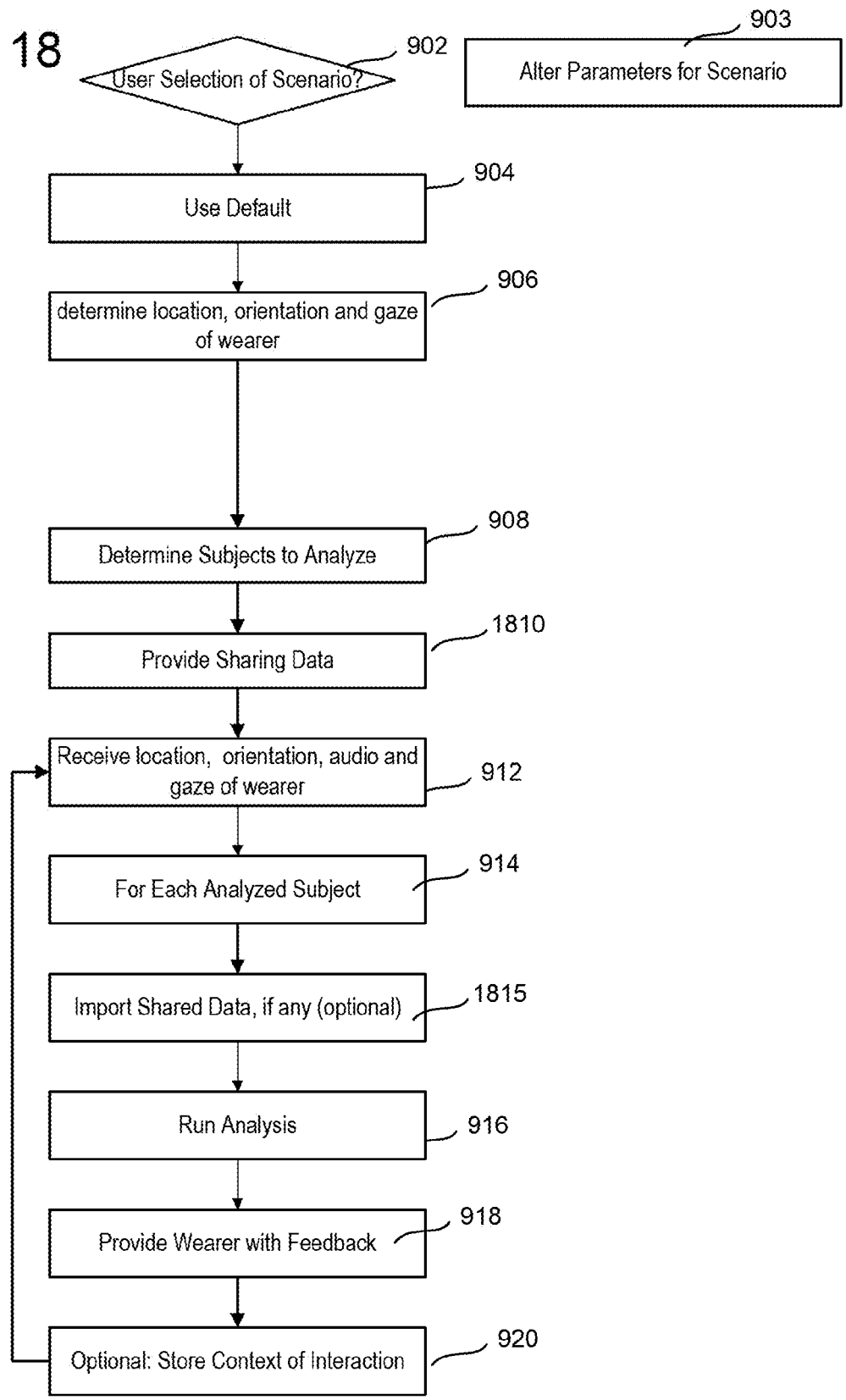

WEARABLE EMOTION DETECTION AND FEEDBACK SYSTEM

PRIORITY CLAIM

This application is a continuation of and claims priority to U.S. patent application Ser. No. 13/665,477, filed Oct. 31, 2012, which is incorporated herein by reference.

BACKGROUND

Mixed reality is a technology that allows virtual imagery to be mixed with a real world physical environment in a display. Systems for mixed reality may include, for example, see through head mounted displays or smart phones with built in cameras. Such systems typically include processing units which provide the imagery under the control of one or more applications.

Emotions have an important influence in human lives, and can influence psychological and social behavior. Humans communicate their emotional state constantly through a variety of verbal and non-verbal behaviors. These expressions can include explicit signals such as smiles and frowns, laughing and crying, to subtle variations in speech rhythm, facial expressions, eye focus or body posture. The range of non-verbal and nonverbal behaviors that transmit information about personality and emotion is large. Emotional arousal affects a number of easily observed behaviors, including speech speed and amplitude, the size and speed of gestures, and some aspects of facial expression and posture. Extensive research has been conducted to correlate observable behaviors with detectable emotional states.

SUMMARY

Technology is described to provide an interpretation of emotional states of subjects within the field of view of a wearer of a see through head mounted display device. A variety of sensors on the display provide input data which is utilized to compute emotional states of subjects within a field of view. During an interaction, the device, recognizes emotional states in subjects by comparing, in real time, detected sensor input against a database of human/primate gestures/expressions, posture, and speech. Feedback is provided to the wearer after interpretation of the sensor input.

A see through head mounted display apparatus included a see-through, head mounted display and sensing devices cooperating with the display to detect audible and visual behaviors of a subject in a field of view of the device. A processing device communicating with display and the sensors monitors audible and visual behaviors of the subject by receiving data from the sensors. Emotional states are computed based on the behaviors and feedback provided to the wearer indicating computed emotional states of the subject.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

FIG. 3A is a flowchart of a method embodiment for aligning a see-through, near-eye, mixed reality display with an IPD.

FIG. 3B is a flowchart of an implementation example of a method for adjusting a display device for bringing the device into alignment with a wearer IPD.

FIG. 3C is a flowchart illustrating different example options of mechanical or automatic adjustment of at least one display adjustment mechanism.

FIG. 4A is a side view of an eyeglass temple in an eyeglasses embodiment of a mixed reality display device providing support for hardware and software components.

FIG. 4B is a side view of an eyeglass temple in an embodiment of a mixed reality display device providing support for hardware and software components and three dimensional adjustment of a microdisplay assembly.

FIG. 5A is a top view of an embodiment of a movable display optical system of a see-through, near-eye, mixed reality device including an arrangement of gaze detection elements.

FIG. 5B is a top view of another embodiment of a movable display optical system of a see-through, near-eye, mixed reality device including an arrangement of gaze detection elements.

FIG. 5C is a top view of a third embodiment of a movable display optical system of a see-through, near-eye, mixed reality device including an arrangement of gaze detection elements.

FIG. 5D is a top view of a fourth embodiment of a movable display optical system of a see-through, near-eye, mixed reality device including an arrangement of gaze detection elements.

FIG. 9 is a flow chart representing a method for providing emotional state feedback to the wear of a head mounted display device.

FIG. 10A is a flow chart illustrating a method for analyzing emotional data.

FIGS. 15A and 15B illustrate types of visual feedback which may be provided to the wearer of a see through head mounted display device.

FIG. 18 illustrates an alternative embodiment of the method for providing emotional feedback where shared data is incorporated into the analysis and provided as part of the feedback to the user.

DETAILED DESCRIPTION

The technology described herein includes a see-through, head mounted display device providing a wearer with detected emotional feedback for interactions the wearer has with other parties within the user's field of view. During an interaction, the device, through a variety of sensors, scans and recognizes emotional states in subjects by comparing, in real time, detected sensor input against the database of human/primate gestures/expressions, posture, and speech. Feedback is provided to the wearer after interpretation of the sensor input. Feedback may comprise a combination of visual or audio feedback which helps the wearer identify positive, neutral, negative emotions in a subject in order facilitate changes in the course of an interaction. The targeted subject or group is constantly analyzed using the see through head mounted display partnered with an emotion detection engine to provide feedback to the wearer (e.g. Happy, interested, flirting, trusting, apprehensive, concerned, etc.). The wearer can then utilize the feedback to help facilitate successful interactions.

FIGS. 1-6 illustrate an exemplary see-through, mixed reality display device suitable for implementing the system.

Figure 1A:
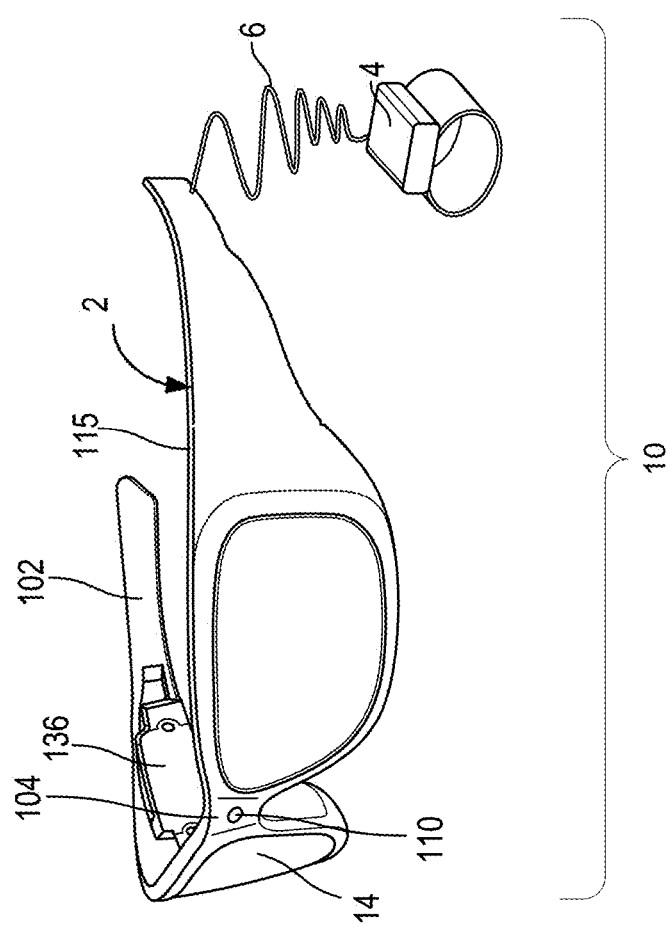
FIG. 1A is a block diagram depicting example components of one embodiment of a see-through, mixed reality display device with adjustable IPD in a system environment in which the device may operate.

FIG. 1A is a block diagram depicting example components of one embodiment of a see-through, mixed reality display device in a system environment in which the device may operate. In one embodiment, the technology implements a see through, near-eye display device. In other embodiments, see through display devices of different types may be used. System 10 includes a see-through display device as a near-eye, head mounted display device 2 in communication with processing unit 4 via wire 6. In other embodiments, head mounted display device 2 communicates with processing unit 4 via wireless communication. Processing unit 4 may take various embodiments. In some embodiments, processing unit 4 is a separate unit which may be worn on the wearer's body, e.g. the wrist in the illustrated example or in a pocket, and includes much of the computing power used to operate near-eye display device 2. Processing unit 4 may communicate wirelessly (e.g., WiFi, Bluetooth, infra-red, or other wireless communication means) to one or more computing systems, hot spots, cellular data networks, etc. In other embodiments, the functionality of the processing unit 4 may be integrated in software and hardware components of the display device 2.

See through head mounted display device 2, which in one embodiment is in the shape of eyeglasses in a frame 115, is worn on the head of a wearer so that the wearer can see through a display, embodied in this example as a display optical system 14 for each eye, and thereby have an actual direct view of the space in front of the wearer. The use of the term "actual direct view" refers to the ability to see real world objects directly with the human eye, rather than seeing created image representations of the objects. For example, looking through glass at a room allows a wearer to have an actual direct view of the room, while viewing a video of a room on a television is not an actual direct view of the room. Based on the context of executing software, for example, a gaming application, the system can project images of virtual objects, sometimes referred to as virtual images or holograms, on the display that are viewable by the person wearing the see-through display device while that person is also viewing real world objects through the display.

Frame 115 provides a support for holding elements of the system in place as well as a conduit for electrical connections. In this embodiment, frame 115 provides a convenient eyeglass frame as support for the elements of the system discussed further below. In other embodiments, other support structures can be used. An example of such a structure is a visor, hat, helmet or goggles. The frame 115 includes a temple or side arm for resting on each of a wearer's ears. Temple 102 is representative of an embodiment of the right temple and includes control circuitry 136 for the display device 2. Nose bridge 104 of the frame includes a microphone 110 for recording sounds and transmitting audio data to processing unit 4.

Figure 1B:
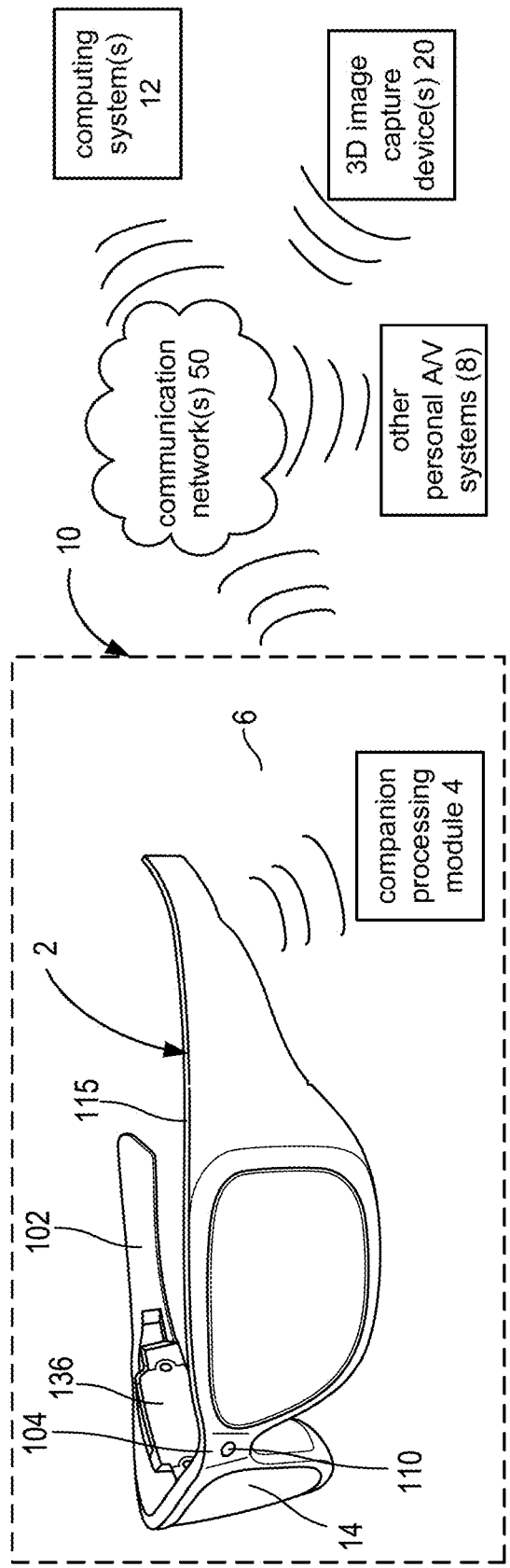
FIG. 1B is a block diagram depicting example components of another embodiment of a see-through, mixed reality display device with adjustable IPD.

FIG. 1B is a block diagram depicting example components of another embodiment of a see-through, mixed reality display device. In some embodiments, processing unit 4 is a separate unit which may be worn on the wearer's body, e.g. a wrist, or be a separate device like a mobile device (e.g. smartphone). The processing unit 4 may communicate wired or wirelessly (e.g., WiFi, Bluetooth, infrared, RFID transmission, wireless Universal Serial Bus (USB), cellular, 3G, 4G or other wireless communication means) over a communication network 50 to one or more computing systems 12 whether located nearby or at a remote location. In other embodiments, the functionality of the processing unit 4 may be integrated in software and hardware components of the display device 2.

Figure 16B:
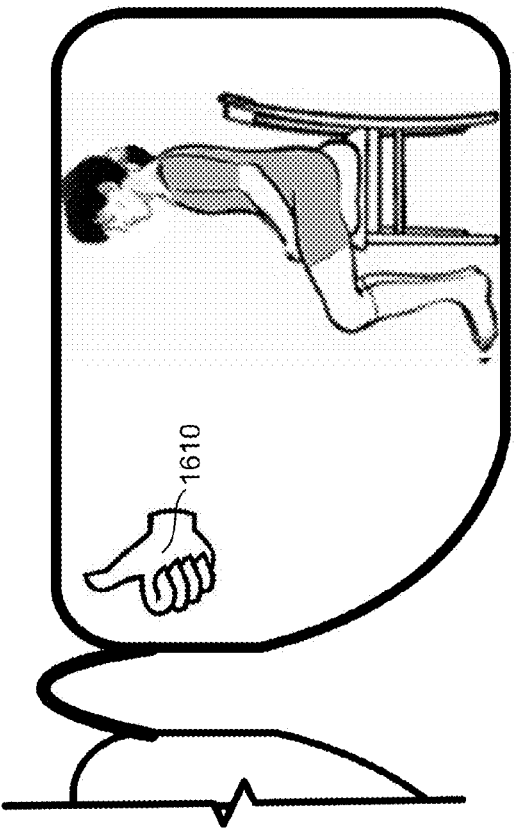
FIGS. 16A and 16B illustrate alternative types of visual feedback which may be provided to the wearer of a see through head mounted display device.

One or more remote, network accessible computer system(s) 12 may be leveraged for processing power and remote data access. An example of hardware components of a computing system 12 is shown in FIG. 16. An application may be executing on computing system 12 which interacts with or performs processing for an application executing on one or more processors in the see-through, augmented reality display system 10. For example, a 3D mapping application may be executing on the one or more computer systems 12 and the wearer's display system 10.

Additionally, in some embodiments, the applications executing on other see through head mounted display systems 10 in same environment or in communication with each other share data updates in real time, for example object identifications and occlusion data like an occlusion volume for a real object, in a peer-to-peer configuration between devices or to object management service executing in one or more network accessible computing systems.

The shared data in some examples may be referenced with respect to one or more referenced coordinate systems accessible to the device 2. In other examples, one head mounted display (HMD) device may receive data from another HMD device including image data or data derived from image data, position data for the sending HMD, e.g. GPS or IR data giving a relative position, and orientation data. An example of data shared between the HMDs is depth map data including image data and depth data captured by its front facing cameras 113, object identification data, and occlusion volumes for real objects in the depth map. The real objects may still be unidentified or have been recognized by software executing on the HMD device or a supporting computer system, e.g. 12 or another display system 10.

An example of an environment is a 360 degree visible portion of a real location in which the wearer is situated. A wearer may be looking at a subset of his environment which is his field of view. For example, a room is an environment. A person may be in a house and be in the kitchen looking at the top shelf of the refrigerator. The top shelf of the refrigerator is within his display field of view, the kitchen is his environment, but his upstairs bedroom is not part of his current environment as walls and a ceiling block his view of the upstairs bedroom. Of course, as he moves, his environment changes. Some other examples of an environment may be a ball field, a street location, a section of a store, a customer section of a coffee shop and the like. A location can include multiple environments, for example, the house may be a location. The wearer and his friends may be wearing their display device systems for playing a game which takes place throughout the house. As each player moves about the house, his environment changes. Similarly, a perimeter around several blocks may be a location and different intersections provide different environments to view as different cross streets come into view. In some instances, a location can also be an environment depending on the precision of location tracking sensors or data.

Figure 2A:
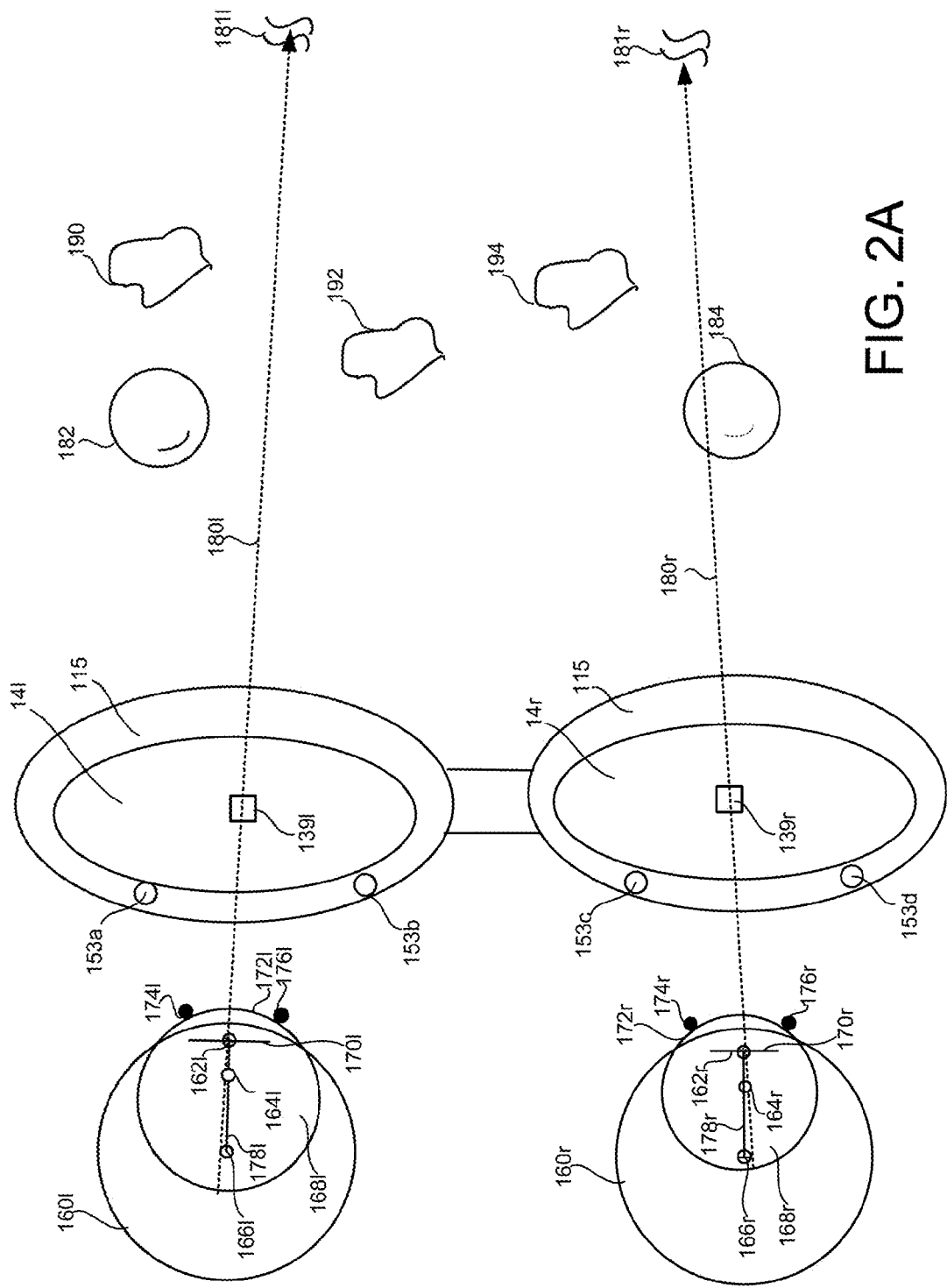
FIG. 2A is a top view illustrating examples of gaze vectors extending to a point of gaze at a distance and a direction for aligning a far IPD.

FIG. 2A is a top view illustrating examples of gaze vectors extending to a point of gaze at a distance and direction for aligning a far inter-pupillary distance (IPD). FIG. 2A illustrates examples of gaze vectors intersecting at a point of gaze where a wearer's eyes are focused effectively at infinity, for example beyond five (5) feet, or, in other words, examples of gaze vectors when the wearer is looking straight ahead. A model of the eyeball 160*l*, 160*r* is illustrated for each eye based on the Gullstrand schematic eye model. For each eye, an eyeball 160 is modeled as a sphere with a center 166 of rotation and includes a cornea 168 modeled as a sphere too and having a center 164. The cornea rotates with the eyeball, and the center 166 of rotation of the eyeball may be treated as a fixed point. The cornea covers an iris 170 with a pupil 162 at its center. In this example, on the surface 172 of the respective cornea are glints 174 and 176.

In the illustrated embodiment of FIG. 2A, a sensor detection area 139 (139*l* and 139*r*) is aligned with the optical axis of each display optical system 14 within an eyeglass frame 115. The sensor associated with the detection area is a camera in this example capable of capturing image data representing glints 174*l* and 176*l* generated respectively by illuminators 153*a* and 153*b* on the left side of the frame 115 and data representing glints 174*r* and 176*r* generated respectively by illuminators 153*c* and 153*d*. Through the display optical systems, 14*l* and 14*r* in the eyeglass frame 115, the wearer's field of view includes both real objects 190, 192 and 194 and virtual objects 182, 184, and 186.

The axis 178 formed from the center 166 of rotation through the cornea center 164 to the pupil 162 is the optical axis of the eye. A gaze vector 180 is sometimes referred to as the line of sight or visual axis which extends from the fovea through the center of the pupil 162. The fovea is a small area of about 1.2 degrees located in the retina. The angular offset between the optical axis computed and the visual axis has horizontal and vertical components. The horizontal component is up to 5 degrees from the optical axis, and the vertical component is between 2 and 3 degrees. In many embodiments, the optical axis is determined and a small correction is determined through wearer calibration to obtain the visual axis which is selected as the gaze vector.

For each wearer, a virtual object may be displayed by the display device at each of a number of predetermined positions at different horizontal and vertical positions. An optical axis may be computed for each eye during display of the object at each position, and a ray modeled as extending from the position into the wearer eye. A gaze offset angle with horizontal and vertical components may be determined based on how the optical axis is to be moved to align with the modeled ray. From the different positions, an average gaze offset angle with horizontal or vertical components can be selected as the small correction to be applied to each computed optical axis. In some embodiments, a horizontal component is used for the gaze offset angle correction.

The gaze vectors 180*l* and 180*r* are not perfectly parallel as the vectors become closer together as they extend from the eyeball into the field of view at a point of gaze which is effectively at infinity as indicated by the symbols 181*l* and 181*r*. At each display optical system 14, the gaze vector 180 appears to intersect the optical axis upon which the sensor detection area 139 is centered. In this configuration, the optical axes are aligned with the inter-pupillary distance (IPD). When a wearer is looking straight ahead, the IPD measured is also referred to as the far IPD.

When identifying an object for a wearer to focus on for aligning IPD at a distance, the object may be aligned in a direction along each optical axis of each display optical system. Initially, the alignment between the optical axis and wearer's pupil is not known. For a far IPD, the direction may be straight ahead through the optical axis. When aligning near IPD, the identified object may be in a direction through the optical axis, however due to vergence of the eyes at close distances, the direction is not straight ahead although it may be centered between the optical axes of the display optical systems.

Figure 2B:
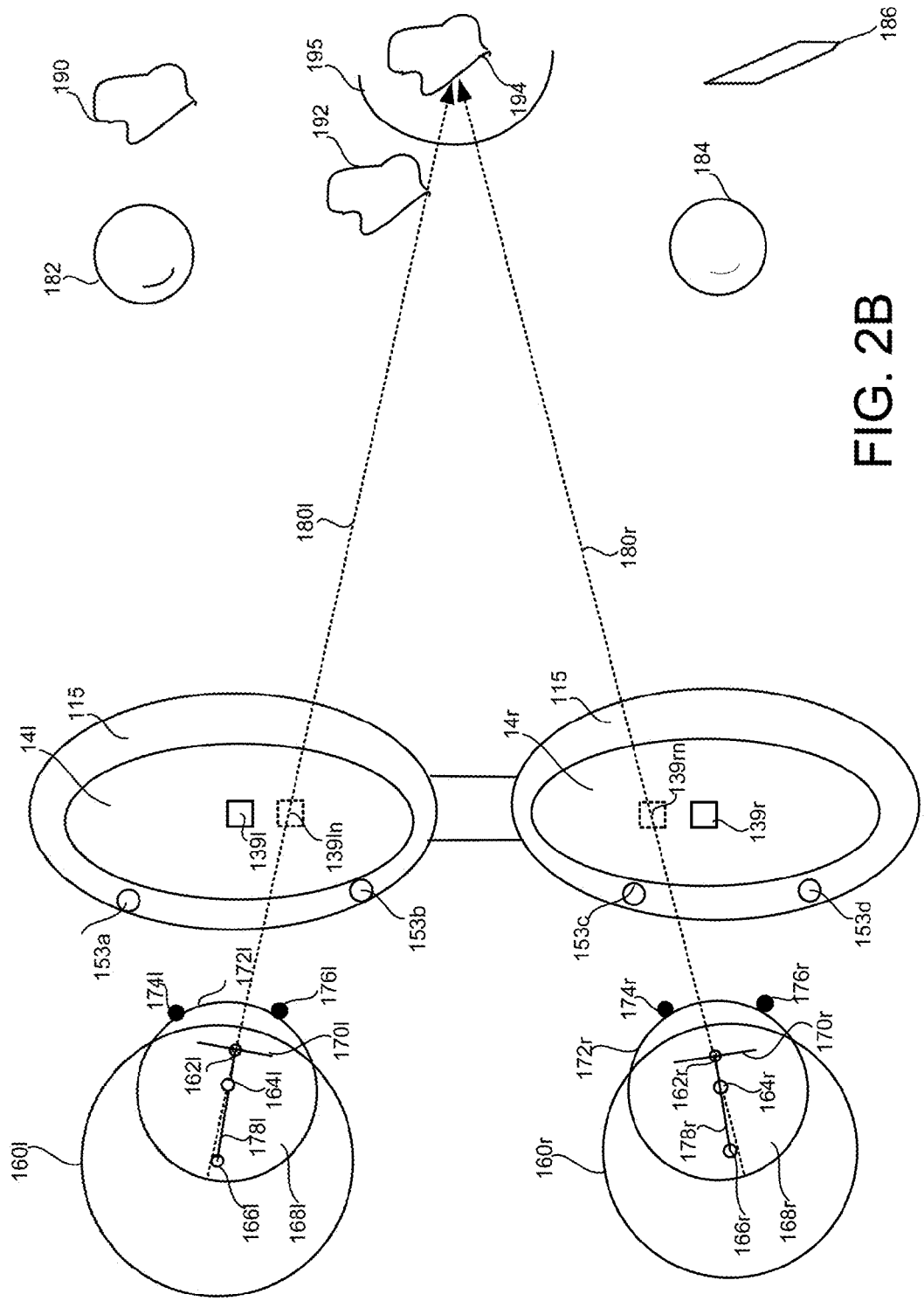
FIG. 2B is a top view illustrating examples of gaze vectors extending to a point of gaze at a distance and a direction for aligning a near IPD.

FIG. 2B is a top view illustrating examples of gaze vectors extending to a point of gaze at a distance and direction for aligning a near IPD. In this example, the cornea 168*l* of the left eye is rotated to the right or towards the wearer's nose, and the cornea 168*r* of the right eye is rotated to the left or towards the wearer's nose. Both pupils are gazing at a real object 194 at a much closer distance, for example two (2) feet in front of the wearer. Gaze vectors 180*l* and 180*r* from each eye enter the Panum's fusional region 195 in which real object 194 is located. The Panum's fusional region is the area of single vision in a binocular viewing system like that of human vision. The intersection of the gaze vectors 180*l* and 180*r* indicates that the wearer is looking at real object 194. At such a distance, as the eyeballs rotate inward, the distance between their pupils decreases to a near IPD. The near IPD is typically about 4 mm less than the far IPD. A near IPD distance criteria, e.g. a point of gaze at less than four feet for example, may be used to switch or adjust the IPD alignment of the display optical systems 14 to that of the near IPD. For the near IPD, each display optical system 14 may be moved toward the wearer's nose so the optical axis, and detection area 139, moves toward the nose a few millimeters as represented by detection areas 139*ln* and 139*rn*.

Techniques for automatically determining a wearer's IPD and automatically adjusting the STHMD to set the IPD for optimal wearer viewing, are discussed in co-pending U.S. patent application Ser. No. 13/221,739 entitled Gaze Detection In A See-Through, Near-Eye, Mixed Reality Display; U.S. patent application Ser. No. 13/221,707 entitled Adjustment Of A Mixed Reality Display For Inter-Pupillary Distance Alignment; and U.S. patent application Ser. No. 13/221,662 entitled Aligning Inter-Pupillary Distance In A Near-Eye Display System, all of which are hereby incorporated specifically by reference.

In general, FIG. 3A shows is a flowchart of a method embodiment 300 for aligning a see-through, near-eye, mixed reality display with an IPD. In step 301, one or more processors of the control circuitry 136, automatically determines whether a see-through, near-eye, mixed reality display device is aligned with an IPD of a wearer in accordance with an alignment criteria. If not, in step 302, the one or more processors cause adjustment of the display device by at least one display adjustment mechanism for bringing the device into alignment with the wearer IPD. If it is determined the see-through, near-eye, mixed reality display device is in alignment with a wearer IPD, optionally, in step 303 an IPD data set is stored for the wearer. In some embodiments, a display device 2 may automatically determine whether there is IPD alignment every time anyone puts on the display device 2. However, as IPD data is generally fixed for adults, due to the confines of the human skull, an IPD data set may be determined typically once and stored for each wearer. The stored IPD data set may at least be used as an initial setting for a display device with which to begin an IPD alignment check.

FIG. 3B is a flowchart of an implementation example of a method for adjusting a display device for bringing the device into alignment with a wearer IPD. In this method, at least one display adjustment mechanism adjusts the position of at least one display optical system 14 which is misaligned. In step 407, one or more adjustment are automatically determined for the at least one display adjustment mechanism for satisfying the alignment criteria for at least one display optical system. In step 408, that at least one display optical system is adjusted based on the one or more adjustment values. The adjustment may be performed automatically under the control of a processor or mechanically as discussed further below.

FIG. 3C is a flowchart illustrating different example options of mechanical or automatic adjustment by the at least one display adjustment mechanism as may be used to implement step 408. Depending on the configuration of the display adjustment mechanism in the display device 2, from step 407 in which the one or more adjustment values were already determined, the display adjustment mechanism may either automatically, meaning under the control of a processor, adjust the at least one display adjustment mechanism in accordance with the one or more adjustment values in step 334. Alternatively, one or more processors associated with the system may electronically provide instructions as per step 333 for wearer application of the one or more adjustment values to the at least one display adjustment mechanism. There may be instances of a combination of automatic and mechanical adjustment under instructions.

Some examples of electronically provided instructions are instructions displayed by the microdisplay 120, the processing unit 4 or audio instructions through speakers 130 of the display device 2. There may be device configurations with an automatic adjustment and a mechanical mechanism depending on wearer preference or for allowing a wearer some additional control.

FIG. 4A illustrates an exemplary arrangement of a see through, near-eye, mixed reality display device embodied as eyeglasses with movable display optical systems including gaze detection elements. What appears as a lens for each eye represents a display optical system 14 for each eye, e.g. 14*r* and 14*l*. A display optical system includes a see-through lens, e.g. 118 and 116 in FIGS. 5A-5*b*, as in an ordinary pair of glasses, but also contains optical elements (e.g. mirrors, filters) for seamlessly fusing virtual content with the actual direct real world view seen through the lenses 118, 116. A display optical system 14 has an optical axis which is generally in the center of the see-through lens 118, 116 in which light is generally collimated to provide a distortionless view. For example, when an eye care professional fits an ordinary pair of eyeglasses to a wearer's face, a goal is that the glasses sit on the wearer's nose at a position where each pupil is aligned with the center or optical axis of the respective lens resulting in generally collimated light reaching the wearer's eye for a clear or distortionless view.

In an exemplary display device 2, a detection area of at least one sensor is aligned with the optical axis of its respective display optical system so that the center of the detection area is capturing light along the optical axis. If the display optical system is aligned with the wearer's pupil, each detection area of the respective sensor is aligned with the wearer's pupil. Reflected light of the detection area is transferred via one or more optical elements to the actual image sensor of the camera in this example illustrated by dashed line as being inside the frame 115.

In one example, a visible light camera (also commonly referred to as an RGB camera) may be the sensor. An example of an optical element or light directing element is a visible light reflecting mirror which is partially transmissive and partially reflective. The visible light camera provides image data of the pupil of the wearer's eye, while IR photodetectors 152 capture glints which are reflections in the IR portion of the spectrum. If a visible light camera is used, reflections of virtual images may appear in the eye data captured by the camera. An image filtering technique may be used to remove the virtual image reflections if desired. An IR camera is not sensitive to the virtual image reflections on the eye.

In other examples, the at least one sensor is an IR camera or a position sensitive detector (PSD) to which the IR radiation may be directed. For example, a hot reflecting surface may transmit visible light but reflect IR radiation. The IR radiation reflected from the eye may be from incident radiation of illuminators, other IR illuminators (not shown) or from ambient IR radiation reflected off the eye. In some examples, sensor may be a combination of an RGB and an IR camera, and the light directing elements may include a visible light reflecting or diverting element and an IR radiation reflecting or diverting element. In some examples, a camera may be small, e.g. 2 millimeters (mm) by 2 mm.

Various types of gaze detection systems are suitable for use in the present system. In some embodiments which calculate a cornea center as part of determining a gaze vector, two glints, and therefore two illuminators will suffice. However, other embodiments may use additional glints in determining a pupil position and hence a gaze vector. As eye data representing the glints is repeatedly captured, for example at 30 frames a second or greater, data for one glint may be blocked by an eyelid or even an eyelash, but data may be gathered by a glint generated by another illuminator.

FIG. 4A is a side view of an eyeglass temple 102 of the frame 115 in an eyeglasses embodiment of a see-through, mixed reality display device. At the front of frame 115 is physical environment facing video camera 113 that can capture video and still images. Particularly in some embodiments, physical environment facing camera 113 may be a depth camera as well as a visible light or RGB camera. For example, the depth camera may include an IR illuminator transmitter and a hot reflecting surface like a hot mirror in front of the visible image sensor which lets the visible light pass and directs reflected IR radiation within a wavelength range or about a predetermined wavelength transmitted by the illuminator to a CCD or other type of depth sensor. Other types of visible light camera (RGB camera) and depth cameras can be used. More information about depth cameras can be found in U.S. patent application Ser. No. 12/813,675, filed on Jun. 11, 2010, incorporated herein by reference in its entirety. The data from the sensors may be sent to a processor 210 of the control circuitry 136, or the processing unit 4 or both which may process them but which the unit 4 may also send to a computer system over a network or secondary computing system for processing. The processing identifies objects through image segmentation and edge detection techniques and maps depth to the objects in the wearer's real world field of view. Additionally, the physical environment facing camera 113 may also include a light meter for measuring ambient light.

Control circuitry 136 provide various electronics that support the other components of head mounted display device 2. More details of control circuitry 136 are provided below with respect to FIGS. 6A and 6B. Inside, or mounted to temple 102, are ear phones 130, inertial sensors 132, GPS transceiver 144 and temperature sensor 138. In one embodiment inertial sensors 132 include a three axis magnetometer 132A, three axis gyro 132B and three axis accelerometer 132C (See FIG. 7A). The inertial sensors are for sensing position, orientation, and sudden accelerations of head mounted display device 2. From these movements, head position may also be determined.

The display device 2 provides an image generation unit which can create one or more images including one or more virtual objects. In some embodiments a microdisplay may be used as the image generation unit. A microdisplay assembly 173 in this example comprises light processing elements and a variable focus adjuster 135. An example of a light processing element is a microdisplay 120. Other examples include one or more optical elements such as one or more lenses of a lens system 122 and one or more reflecting elements such as reflective elements 124a and 124b in FIGS. 6A and 6B or 124 in FIGS. 6C and 6D. Lens system 122 may comprise a single lens or a plurality of lenses.

Mounted to or inside temple 102, the microdisplay 120 includes an image source and generates an image of a virtual object. The microdisplay 120 is optically aligned with the lens system 122 and the reflecting element 124 or reflecting elements 124a and 124b as illustrated in the following Figures. The optical alignment may be along an optical path 133 including one or more optical axes. The microdisplay 120 projects the image of the virtual object through lens system 122, which may direct the image light, onto reflecting element 124 which directs the light into lightguide optical element 112 as in FIGS. 5C and 5D or onto reflecting element 124a (e.g. a mirror or other surface) which directs the light of the virtual image to a partially reflecting element 124b which combines the virtual image view along path 133 with the natural or actual direct view along the optical axis 142 as in FIGS. 5A-5D. The combination of views are directed into a wearer's eye.

The variable focus adjuster 135 changes the displacement between one or more light processing elements in the optical path of the microdisplay assembly or an optical power of an element in the microdisplay assembly. The optical power of a lens is defined as the reciprocal of its focal length, e.g. 1/focal length, so a change in one effects the other. The change in focal length results in a change in the region of the field of view, e.g. a region at a certain distance, which is in focus for an image generated by the microdisplay assembly 173.

In one example of the microdisplay assembly 173 making displacement changes, the displacement changes are guided within an armature 137 supporting at least one light processing element such as the lens system 122 and the microdisplay 120 in this example. The armature 137 helps stabilize the alignment along the optical path 133 during physical movement of the elements to achieve a selected displacement or optical power. In some examples, the adjuster 135 may move one or more optical elements such as a lens in lens system 122 within the armature 137. In other examples, the armature may have grooves or space in the area around a light processing element so it slides over the element, for example, microdisplay 120, without moving the light processing element. Another element in the armature such as the lens system 122 is attached so that the system 122 or a lens within slides or moves with the moving armature 137. The displacement range is typically on the order of a few millimeters (mm). In one example, the range is 1-2 mm. In other examples, the armature 137 may provide support to the lens system 122 for focal adjustment techniques involving adjustment of other physical parameters than displacement. An example of such a parameter is polarization.

For more information on adjusting a focal distance of a microdisplay assembly, see U.S. Pat. No. 12/941,825 entitled "Automatic Variable Virtual Focus for Augmented Reality Displays," filed Nov. 8, 2010, having inventors Avi Bar-Zeev and John Lewis and which is hereby incorporated by reference.

In one example, the adjuster 135 may be an actuator such as a piezoelectric motor. Other technologies for the actuator may also be used and some examples of such technologies are a voice coil formed of a coil and a permanent magnet, a magnetostriction element, and an electrostriction element.

There are different image generation technologies that can be used to implement microdisplay 120. For example, microdisplay 120 can be implemented using a transmissive projection technology where the light source is modulated by optically active material, backlit with white light. These technologies are usually implemented using LCD type displays with powerful backlights and high optical energy densities. Microdisplay 120 can also be implemented using a reflective technology for which external light is reflected and modulated by an optically active material. The illumination is forward lit by either a white source or RGB source, depending on the technology. Digital light processing (DLP), liquid crystal on silicon (LCOS) and Mirasol® display technology from Qualcomm, Inc. are all examples of reflective technologies which are efficient as most energy is reflected away from the modulated structure and may be used in the system described herein. Additionally, microdisplay 120 can be implemented using an emissive technology where light is generated by the display. For example, a PicoP™ engine from Microvision, Inc. emits a laser signal with a micro mirror steering either onto a tiny screen that acts as a transmissive element or beamed directly into the eye (e.g., laser).

FIG. 4B is a side view of an eyeglass temple in another embodiment of a mixed reality display device providing support for hardware and software components and three dimensional adjustment of a microdisplay assembly. Some of the numerals illustrated in the FIG. 5A above have been removed to avoid clutter in the drawing. In embodiments where the display optical system 14 is moved in any of three dimensions, the optical elements represented by reflecting element 124 and the other elements of the microdisplay assembly 173, e.g. 120, 122 may also be moved for maintaining the optical path 133 of the light of a virtual image to the display optical system. An XYZ transport mechanism in this example made up of one or more motors represented by display adjustment mechanism 203 and shafts 205 under control of the processor 210 of control circuitry 136 (see FIG. 6A) control movement of the elements of the microdisplay assembly 173. An example of motors which may be used are piezoelectric motors. In the illustrated example, one motor is attached to the armature 137 and moves the variable focus adjuster 135 as well, and another display adjustment mechanism 203 controls the movement of the reflecting element 124.

FIG. 5A is a top view of an embodiment of a movable display optical system 14 of a see-through, near-eye, mixed reality device 2 including an arrangement of gaze detection elements. A portion of the frame 115 of the near-eye display device 2 will surround a display optical system 14 and provides support for elements of an embodiment of a microdisplay assembly 173 including microdisplay 120 and its accompanying elements as illustrated. In order to show the components of the display system 14, in this case display optical system 14r for the right eye system, a top portion of the frame 115 surrounding the display optical system is not depicted. Additionally, the microphone 110 in bridge 104 is not shown in this view to focus attention on the operation of the display adjustment mechanism 203. As in the example of FIG. 4C, the display optical system 14 in this embodiment is moved by moving an inner frame 117r, which in this example surrounds the microdisplay assembly 173 as well. The display adjustment mechanism 203 is embodied in this embodiment provided as three axis motors which attach their shafts 205 to inner frame 117r to translate the display optical system 14, which in this embodiment includes the microdisplay assembly 173, in any of three dimensions as denoted by symbol 145 indicating three (3) axes of movement.

The display optical system 14 in this embodiment has an optical axis 142 and includes a see-through lens 118 allowing the wearer an actual direct view of the real world. In this example, the see-through lens 118 is a standard lens used in eye glasses and can be made to any prescription (including no prescription). In another embodiment, see-through lens 118 can be replaced by a variable prescription lens. In some embodiments, see-through, near-eye display device 2 will include additional lenses.

The display optical system 14 further comprises reflecting reflective elements 124a and 124b. In this embodiment, light from the microdisplay 120 is directed along optical path 133 via a reflecting element 124a to a partially reflective element 124b embedded in lens 118 which combines the virtual object image view traveling along optical path 133 with the natural or actual direct view along the optical axis 142 so that the combined views are directed into a wearer's eye, right one in this example, at the optical axis, the position with the most collimated light for a clearest view.

A detection area of a light sensor is also part of the display optical system 14r. An optical element 125 embodies the detection area by capturing reflected light from the wearer's eye received along the optical axis 142 and directs the captured light to the sensor 134r, in this example positioned in the lens 118 within the inner frame 117r. As shown, the arrangement allows the detection area 139 of the sensor 134r to have its center aligned with the center of the display optical system 14. For example, if sensor 134r is an image sensor, sensor 134r captures the detection area 139, so an image captured at the image sensor is centered on the optical axis because the detection area 139 is. In one example, sensor 134r is a visible light camera or a combination of RGB/IR camera, and the optical element 125 includes an optical element which reflects visible light reflected from the wearer's eye, for example a partially reflective mirror.

In other embodiments, the sensor 134r is an IR sensitive device such as an IR camera, and the element 125 includes a hot reflecting surface which lets visible light pass through it and reflects IR radiation to the sensor 134r. An IR camera may capture not only glints, but also an infra-red or near infra-red image of the wearer's eye including the pupil.

In other embodiments, the IR sensor 134r is a position sensitive device (PSD), sometimes referred to as an optical position sensor. The depiction of the light directing elements, in this case reflecting elements, 125, 124, 124a and 124b in FIGS. 5A-5D are representative of their functions. The elements may take any number of forms and be implemented with one or more optical components in one or more arrangements for directing light to its intended destination such as a camera sensor or a wearer's eye.

Figure 6A:
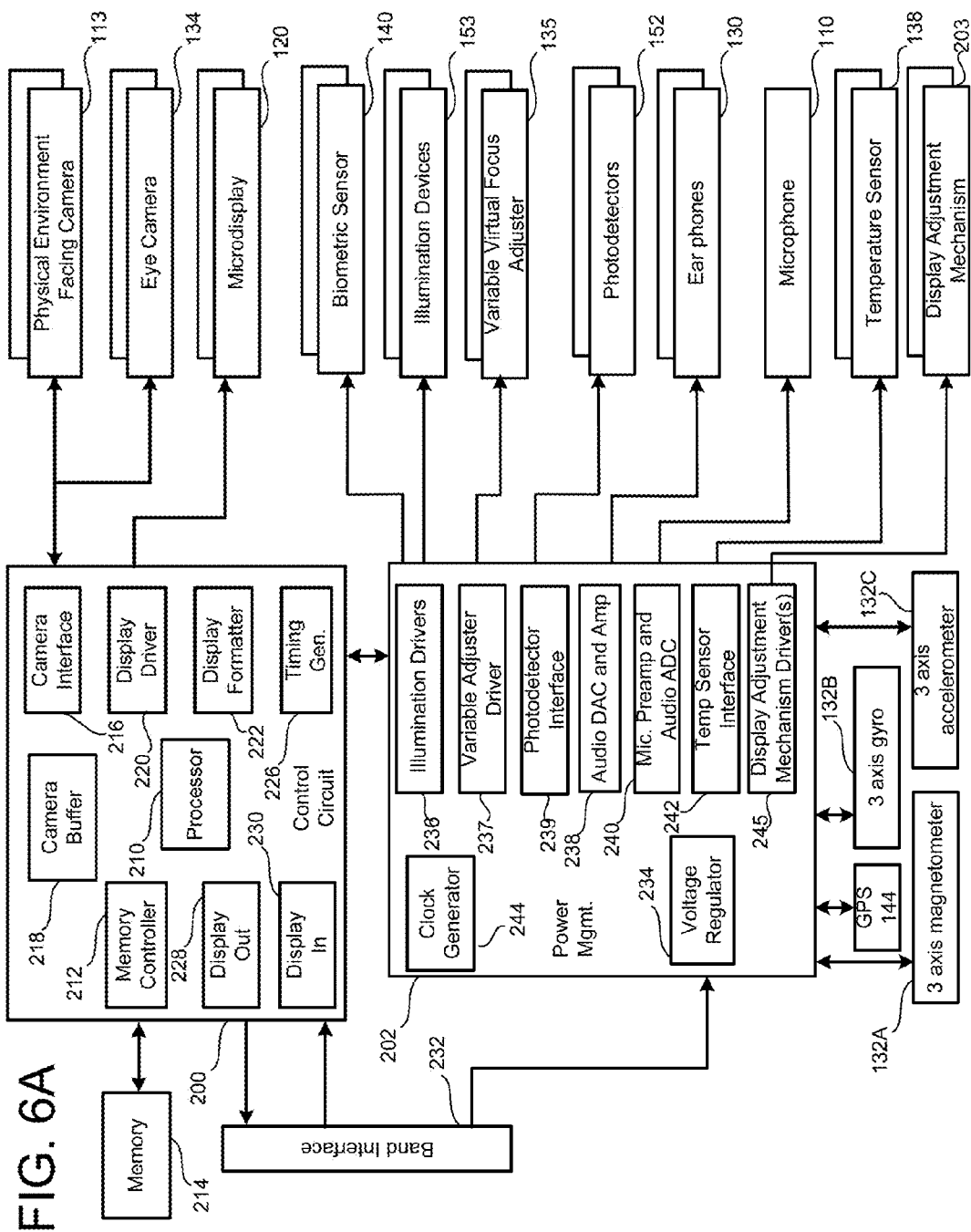
FIG. 6A is a block diagram of one embodiment of hardware and software components of a see-through, near-eye, mixed reality display unit as may be used with one or more embodiments.

As discussed in FIGS. 2A and 2B above and in the Figures below, when the wearer is looking straight ahead, and the center of the wearer's pupil is centered in an image captured of the wearer's eye when a detection area 139 or an image sensor 134r is effectively centered on the optical axis of the display, the display optical system 14r is aligned with the pupil. When both display optical systems 14 are aligned with their respective pupils, the distance between the optical centers matches or is aligned with the wearer's inter-pupillary distance. In the example of FIG. 6A, the inter-pupillary distance can be aligned with the display optical systems 14 in three dimensions.

In one embodiment, if the data captured by the sensor 134 indicates the pupil is not aligned with the optical axis, one or more processors in the processing unit 4 or the control circuitry 136 or both use a mapping criteria which correlates a distance or length measurement unit to a pixel or other discrete unit or area of the image for determining how far off the center of the pupil is from the optical axis 142. Based on the distance determined, the one or more processors determine adjustments of how much distance and in which direction the display optical system 14r is to be moved to align the optical axis 142 with the pupil. Control signals are applied by one or more display adjustment mechanism drivers 245 to each of the components, e.g. display adjustment mechanism 203, making up one or more display adjustment mechanisms 203. In the case of motors in this example, the motors move their shafts 205 to move the inner frame 117r in at least one direction indicated by the control signals. On the temple side of the inner frame 117r are flexible sections 215a, 215b of the frame 115 which are attached to the inner frame 117r at one end and slide within grooves 217a and 217b within the interior of the temple frame 115 to anchor the inner frame 117 to the frame 115 as the display optical system 14 is move in any of three directions for width, height or depth changes with respect to the respective pupil.

In addition to the sensor, the display optical system 14 includes other gaze detection elements. In this embodiment, attached to frame 117r on the sides of lens 118, are at least two (2) but may be more, infra-red (IR) illuminators 153 which direct narrow infra-red light beams within a particular wavelength range or about a predetermined wavelength at the wearer's eye to each generate a respective glint on a surface of the respective cornea. In other embodiments, the illuminators and any photodiodes may be on the lenses, for example at the corners or edges. In this embodiment, in addition to the at least 2 infra-red (IR) illuminators 153 are IR photodetectors 152. Each photodetector 152 is sensitive to IR radiation within the particular wavelength range of its corresponding IR illuminator 153 across the lens 118 and is positioned to detect a respective glint. As shown in FIGS. 4A-4C, the illuminator and photodetector are separated by a barrier 154 so that incident IR light from the illuminator 153 does not interfere with reflected IR light being received at the photodetector 152. In the case where the sensor 134 is an IR sensor, the photodetectors 152 may not be needed or may be an additional glint data capture source. With a visible light camera, the photodetectors 152 capture light from glints and generate glint intensity values.

In FIGS. 5A-5D, the positions of the gaze detection elements, e.g. the detection area 139 and the illuminators 153 and photodetectors 152 are fixed with respect to the optical axis of the display optical system 14. These elements may move with the display optical system 14r, and hence its optical axis, on the inner frame, but their spatial relationship to the optical axis 142 does not change.

FIG. 5B is a top view of another embodiment of a movable display optical system of a see-through, near-eye, mixed reality device including an arrangement of gaze detection elements. In this embodiment, light sensor 134r may be embodied as a visible light camera, sometimes referred to as an RGB camera, or it may be embodied as an IR camera or a camera capable of processing light in both the visible and IR ranges, e.g. a depth camera. In this example, the image sensor 134r is the detection area 139r. The image sensor 134 of the camera is located vertically on the optical axis 142 of the display optical system. In some examples, the camera may be located on frame 115 either above or below see-through lens 118 or embedded in the lens 118. In some embodiments, the illuminators 153 provide light for the camera, and in other embodiments the camera captures images with ambient lighting or light from its own light source. Image data captured may be used to determine alignment of the pupil with the optical axis. Gaze determination techniques based on image data, glint data or both may be used based on the geometry of the gaze detection elements.

In this example, the display adjustment mechanism 203 in bridge 104 moves the display optical system 14r in a horizontal direction with respect to the wearer's eye as indicated by directional symbol 145. The flexible frame portions 215a and 215b slide within grooves 217a and 217b as the system 14 is moved. In this example, reflecting element 124a of a microdisplay assembly 173 embodiment is stationery. As the IPD is typically determined once and stored, any adjustment of the focal length between the microdisplay 120 and the reflecting element 124a that may be done may be accomplished by the microdisplay assembly, for example via adjustment of the microdisplay elements within the armature 137.

FIG. 5C is a top view of a third embodiment of a movable display optical system of a see-through, near-eye, mixed reality device including an arrangement of gaze detection elements. The display optical system 14 has a similar arrangement of gaze detection elements including IR illuminators 153 and photodetectors 152, and a light sensor 134r located on the frame 115 or lens 118 below or above optical axis 142. In this example, the display optical system 14 includes a light guide optical element 112 as the reflective element for directing the images into the wearer's eye and is situated between an additional see-through lens 116 and see-through lens 118. As reflecting element 124 is within the lightguide optical element and moves with the element 112, an embodiment of a microdisplay assembly 173 is attached on the temple 102 in this example to a display adjustment mechanism 203 for the display optical system 14 embodied as a set of three axis mechanism 203 with shafts 205 include at least one for moving the microdisplay assembly. One or more display adjustment mechanism 203 on the bridge 104 are representative of the other components of the display adjustment mechanism 203 which provides three axes of movement. In another embodiment, the display adjustment mechanism may operate to move the devices via their attached shafts 205 in the horizontal direction. The mechanism 203 for the microdisplay assembly 173 would also move it horizontally for maintaining alignment between the light coming out of the microdisplay 120 and the reflecting element 124. A processor 210 of the control circuitry (see FIG. 7A) coordinates their movement.

Lightguide optical element 112 transmits light from microdisplay 120 to the eye of the wearer wearing head mounted display device 2. Lightguide optical element 112 also allows light from in front of the head mounted display device 2 to be transmitted through lightguide optical element 112 to the wearer's eye thereby allowing the wearer to have an actual direct view of the space in front of head mounted display device 2 in addition to receiving a virtual image from microdisplay 120. Thus, the walls of lightguide optical element 112 are see-through. Lightguide optical element 112 includes a first reflecting element 124 (e.g., a mirror or other surface). Light from microdisplay 120 passes through lens system 122 and becomes incident on reflecting element 124. The reflecting element 124 reflects the incident light from the microdisplay 120 such that light is trapped inside a planar, substrate comprising lightguide optical element 112 by internal reflection.

After several reflections off the surfaces of the substrate, the trapped light waves reach an array of selectively reflecting surfaces 126. Note that only one of the five surfaces 126 to prevent over-crowding of the drawing. Reflecting surfaces 126 couple the light waves incident upon those reflecting surfaces out of the substrate into the eye of the wearer. More details of a lightguide optical element can be found in United States Patent Application Publication 2008/0285140, Ser. No. 12/214,366, published on Nov. 20, 2008, "Substrate-Guided Optical Devices" incorporated herein by reference in its entirety. In one embodiment, each eye will have its own lightguide optical element 112.

FIG. 5D is a top view of a fourth embodiment of a movable display optical system of a see-through, near-eye, mixed reality device including an arrangement of gaze detection elements. This embodiment is similar to FIG. 5C's embodiment including a light guide optical element 112. However, the only light detectors are the IR photodetectors 152, so this embodiment relies on glint detection only for gaze detection as discussed in the examples below.

In the embodiments of FIGS. 5A-5D, the positions of the gaze detection elements, e.g. the detection area 139 and the illuminators 153 and photodetectors 152 are fixed with respect to each other. In these examples, they are also fixed in relation to the optical axis of the display optical system 14.

In the embodiments above, the specific number of lenses shown are just examples. Other numbers and configurations of lenses operating on the same principles may be used. Additionally, in the examples above, only the right side of the see-through, near-eye display device 2 are shown. A full near-eye, mixed reality display device would include as examples another set of lenses 116 and/or 118, another lightguide optical element 112 for the embodiments of FIGS. 5C and 5D, another microdisplay 120, another lens system 122, likely another environment facing camera 113, another eye tracking sensor 134 for the embodiments of FIGS. 6A to 6C, earphones 130, and a temperature sensor 138.

Figure 6B:
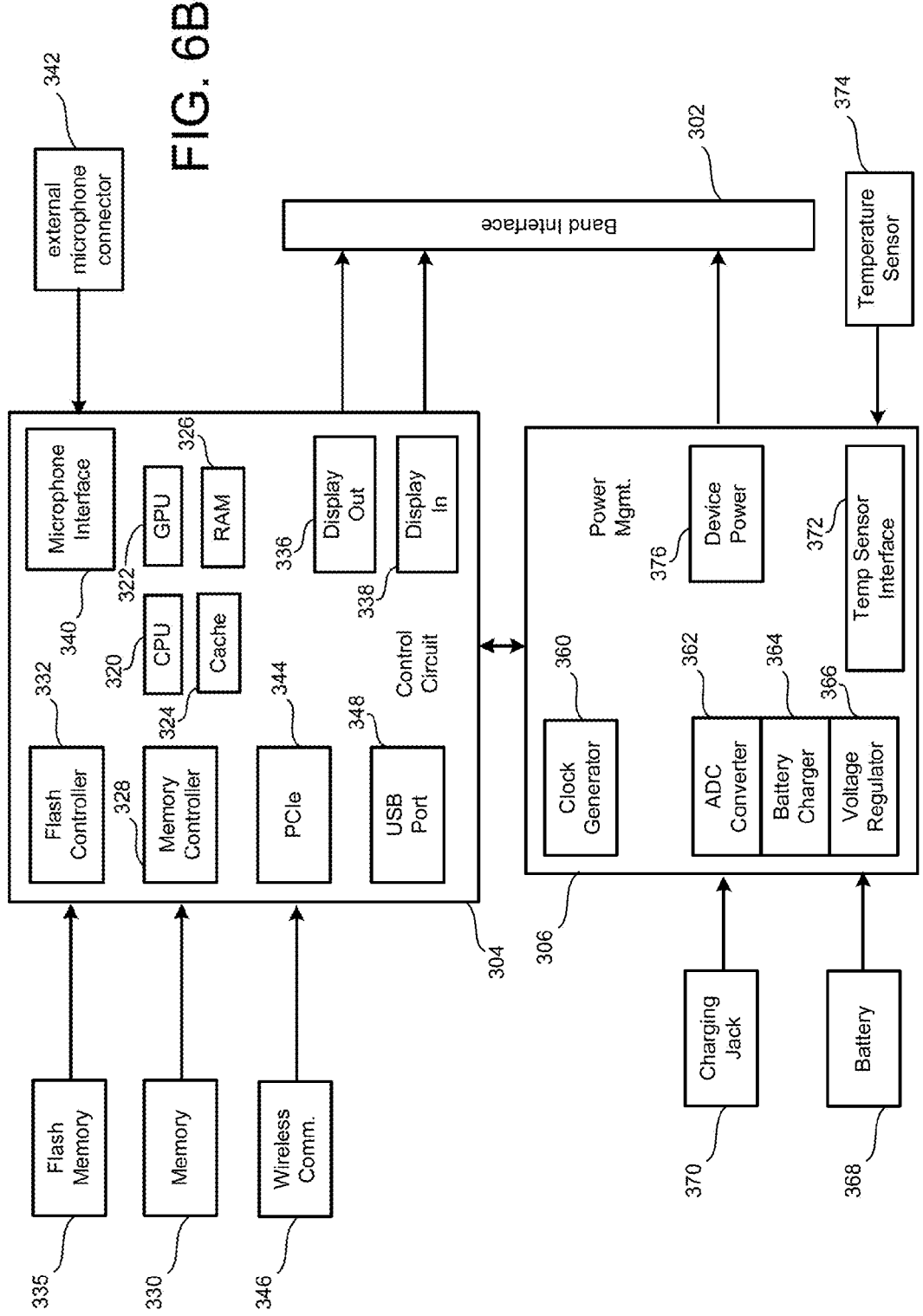
FIG. 6B is a block diagram of one embodiment of the hardware and software components of a processing unit associated with a see though, head mounted display device.

FIG. 6A is a block diagram of one embodiment of hardware and software components of a see-through, near-eye, mixed reality display unit 2 as may be used with one or more embodiments. FIG. 7B is a block diagram describing the various components of a processing unit 4. In this embodiment, near-eye display device 2, receives instructions about a virtual image from processing unit 4 and provides the sensor information back to processing unit 4. Software and hardware components which may be embodied in a processing unit 4 are depicted in FIG. 6B, will receive the sensory information from the display device 2 (See FIG. 1A). Based on that information, processing unit 4 will determine where and when to provide a virtual image to the wearer and send instructions accordingly to the control circuitry 136 of the display device 2.

Note that some of the components of FIG. 6A (e.g., physical environment facing camera 113, eye sensor 134, variable virtual focus adjuster 135, detection area 139, microdisplay 120, illuminators 153, earphones 130, temperature sensor 138, display adjustment mechanism 203) are shown in shadow to indicate that there are at least two of each of those devices, at least one for the left side and at least one for the right side of head mounted display device 2. FIG. 6A shows the control circuit 200 in communication with the power management unit 202. Control circuit 200 includes processor 210, memory controller 212 in communication with memory 214 (e.g., D-RAM), camera interface 216, camera buffer 218, display driver 220, display formatter 222, timing generator 226, display out 228, and display in interface 230. In one embodiment, all of components of driver 220 are in communication with each other via dedicated lines of one or more buses. In another embodiment, each of the components of control circuit 200 are in communication with processor 210.

Camera interface 216 provides an interface to the two physical environment facing cameras 113 and each eye sensor 134 and stores respective images received from the cameras 113, sensor 134 in camera buffer 218. Display driver 220 will drive microdisplay 120. Display formatter 222 may provide information, about the virtual image being displayed on microdisplay 120 to one or more processors of one or more computer systems, e.g. 4, 210 performing processing for the augmented reality system. Timing generator 226 is used to provide timing data for the system. Display out 228 is a buffer for providing images from physical environment facing cameras 113 and the eye sensors 134 to the processing unit 4. Display in 230 is a buffer for receiving images such as a virtual image to be displayed on microdisplay 120. Display out 228 and display in 230 communicate with band interface 232 which is an interface to processing unit 4.

Power management unit 202 includes voltage regulator 234, eye tracking illumination driver 236, variable adjuster driver 237, photodetector interface 239, audio DAC and amplifier 238, microphone preamplifier and audio ADC 240, temperature sensor interface 242, display adjustment mechanism driver(s) 245 and clock generator 244. Voltage regulator 234 receives power from processing unit 4 via band interface 232 and provides that power to the other components of head mounted display device 2. Illumination driver 236 controls, for example via a drive current or voltage, the illuminators 153 to operate about a predetermined wavelength or within a wavelength range. Audio DAC and amplifier 238 receives the audio information from earphones 130. Microphone preamplifier and audio ADC 240 provides an interface for microphone 110. Temperature sensor interface 242 is an interface for temperature sensor 138. One or more display adjustment drivers 245 provide control signals to one or more motors or other devices making up each display adjustment mechanism 203 which represent adjustment amounts of movement in at least one of three directions. Power management unit 202 also provides power and receives data back from three axis magnetometer 132A, three axis gyro 132B and three axis accelerometer 132C. Power management unit 202 also provides power and receives data back from and sends data to GPS transceiver 144. In one embodiment, a biometric sensor 140 including for example a heartbeat sensor may be provided.

The variable adjuster driver 237 provides a control signal, for example a drive current or a drive voltage, to the adjuster 135 to move one or more elements of the microdisplay assembly 173 to achieve a displacement for a focal region calculated by software executing in a processor 210 of the control circuitry 13, or the processing unit 4, or both. In embodiments of sweeping through a range of displacements and, hence, a range of focal regions, the variable adjuster driver 237 receives timing signals from the timing generator 226, or alternatively, the clock generator 244 to operate at a programmed rate or frequency.

The photodetector interface 239 performs any analog to digital conversion needed for voltage or current readings from each photodetector, stores the readings in a processor readable format in memory via the memory controller 212, and monitors the operation parameters of the photodetectors 152 such as temperature and wavelength accuracy.

FIG. 6B is a block diagram of one embodiment of the hardware and software components of a processing unit 4 associated with a see-through, near-eye, mixed reality display unit. The processing unit 4 may include this embodiment of hardware and software components as well as similar components which perform similar functions. FIG. 6B shows controls circuit 304 in communication with power management circuit 306. Control circuit 304 includes a central processing unit (CPU) 320, graphics processing unit (GPU) 322, cache 324, RAM 326, memory control 328 in communication with memory 330 (e.g., D-RAM), flash memory controller 332 in communication with flash memory 335 (or other type of non-volatile storage), display out buffer 336 in communication with see-through, near-eye display device 2 via band interface 302 and band interface 232, display in buffer 338 in communication with near-eye display device 2 via band interface 302 and band interface 232, microphone interface 340 in communication with an external microphone connector 342 for connecting to a microphone, PCI express interface for connecting to a wireless communication component 346, and USB port(s) 348.

In one embodiment, wireless communication component 346 can include a Wi-Fi enabled communication device, Bluetooth communication device, infrared communication device, etc. The USB port can be used to dock the processing unit 4 to a secondary computing device in order to load data or software onto processing unit 4, as well as charge processing unit 4. In one embodiment, CPU 320 and GPU 322 are the main workhorses for determining where, when and how to insert images into the view of the wearer.

Power management circuit 306 includes clock generator 360, analog to digital converter 362, battery charger 364, voltage regulator 366, see-through, near-eye display power interface 376, and temperature sensor interface 372 in communication with temperature sensor 374 (located on the wrist band of processing unit 4). An alternating current to digital converter 362 is connected to a charging jack 370 for receiving an AC supply and creating a DC supply for the system. Voltage regulator 366 is in communication with battery 368 for supplying power to the system. Battery charger 364 is used to charge battery 368 (via voltage regulator 366) upon receiving power from charging jack 370. Device power interface 376 provides power to the display device 2.

The system described above can be used to add virtual images to a wearer's view such that the virtual images are mixed with real images that the wearer see. In one example, the virtual images are added in a manner such that they appear to be part of the original scene. Examples of adding the virtual images can be found U.S. patent application Ser. No. 13/112,919, "Event Augmentation With Real-Time Information," filed on May 20, 2011; and U.S. patent application Ser. No. 12/905,952, "Fusing Virtual Content Into Real Content," filed on Oct. 15, 2010; both applications are incorporated herein by reference in their entirety.

To provide a mixed reality environment wherein virtual objects rendered by a display device interact with real objects in the field of view of a wearer, an object-centric tracking system is implemented. The object-centric tracking system uses a standard definition for each instance of a real world object and a rendered virtual object. This allows each processing unit 4 and computing system 12 to understand and process objects, both real and virtual, in a manner that is consistent across all devices and allows each rendering device to perform the calculations to render correct interactions between the objects in the field of view.

Figure 7A:
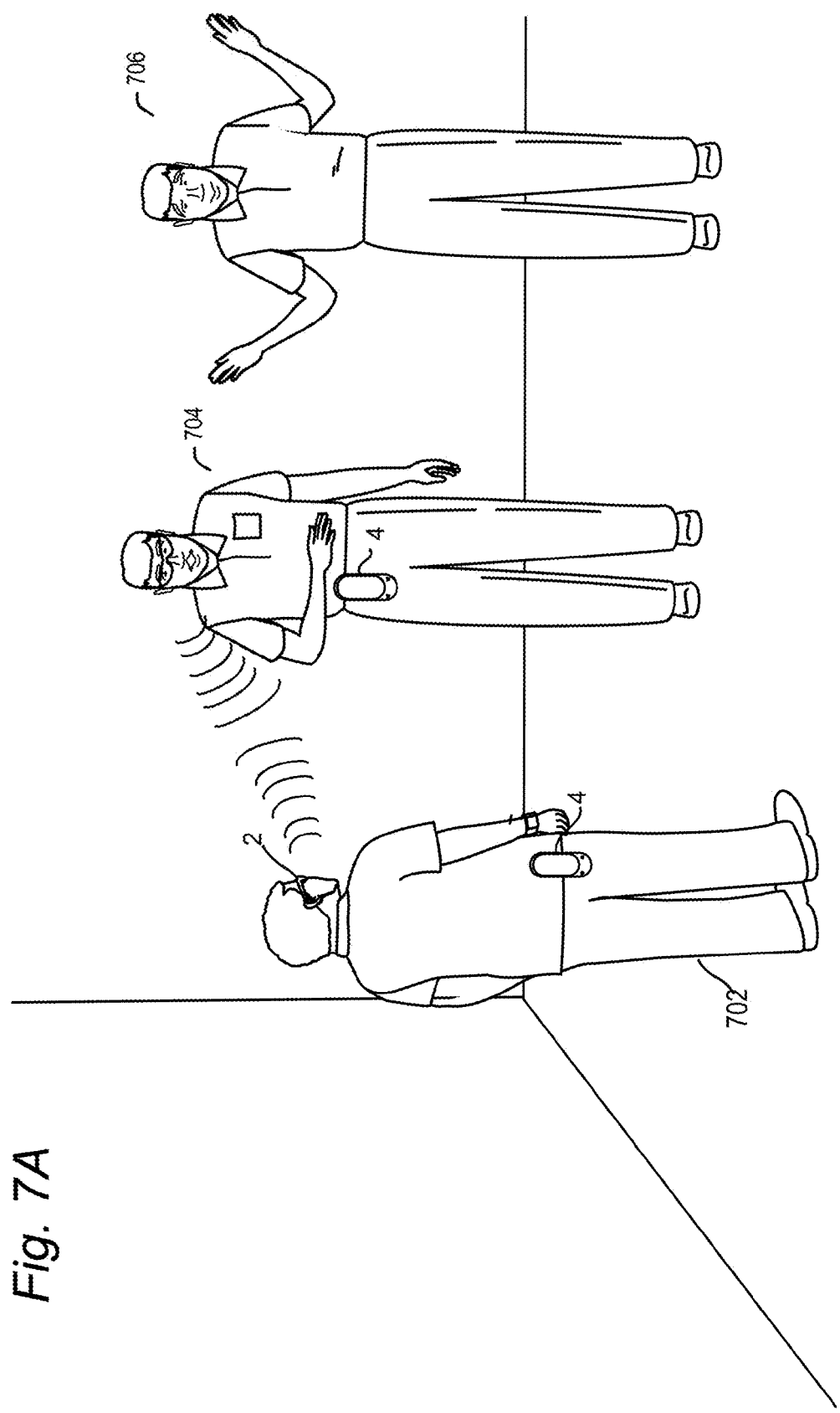
FIG. 7A is a depiction of a personal interaction between a wearer of a see though, head mounted display device.
Figure 7B:
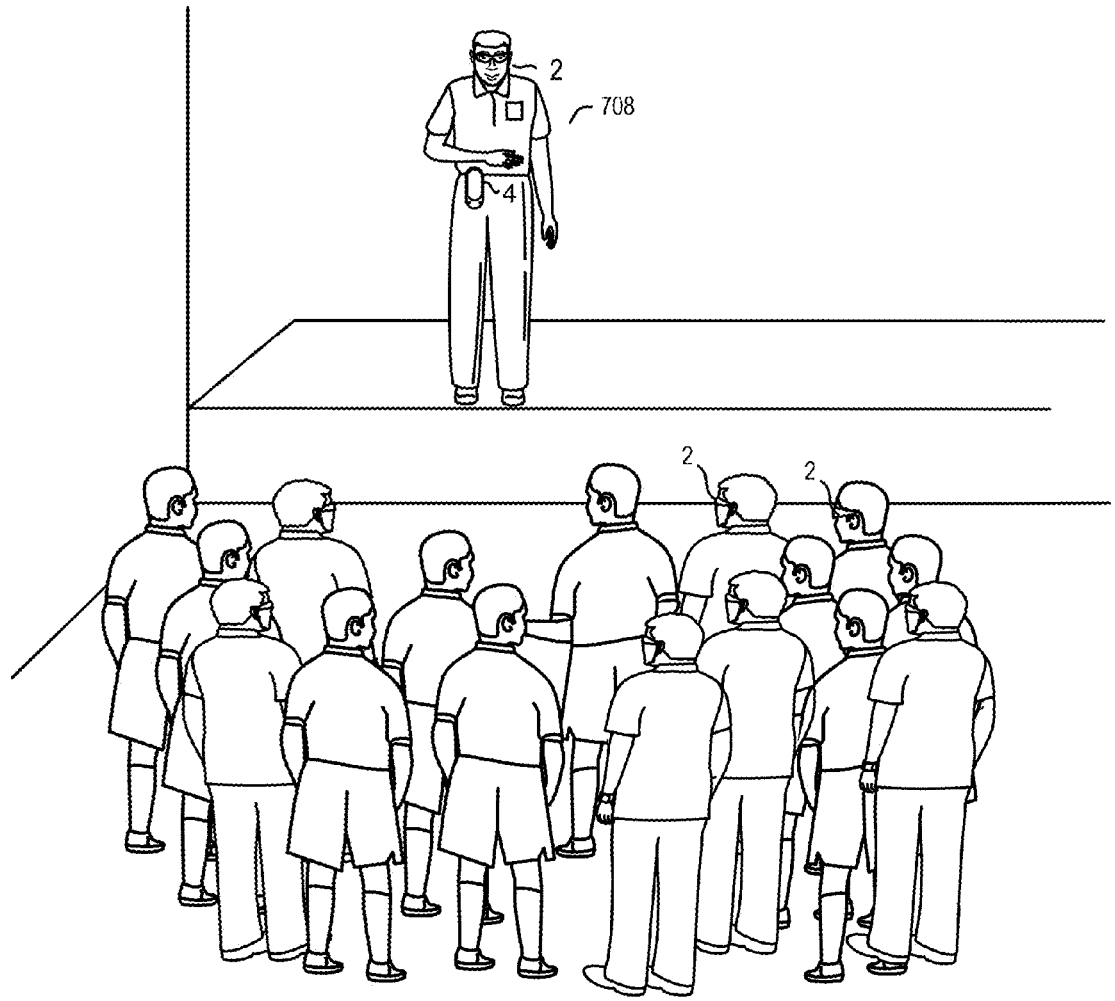
FIG. 7B is a depiction of a presentation made by a wearer for a see though, head mounted display device.

FIGS. 7A and 7b illustrate social and business interactions within which a wearer of a see though head mounted display may interact with other individuals. In FIG. 7A, a first individual 702 is conversing with a second individual 704. In one aspect, the conversation may include expressions and gestures on the part of two interacting individuals 702 and 704. One or both individuals may have a see through head mounted display, and in FIG. 7A both individuals 702 and 704 possesses a device 2. Another individual 706 is exhibiting gestures while listening to the individual 702. Individuals 702 and 704 each possess a see through head mounted display device 2, while individual 706 does not.

During an interaction between individuals 702 and 704, each device 2, worn by individuals 702 and 704 can interpret visual and audio input, interpret emotional states exhibited by other individuals within a wearer's field of view, and provide the wearer with feedback regarding the subject's emotional state. Gestures expressed by subject 706 such as raising the subject's arms and expressions on the user's face are detectable by the device 2. Each of these particular behaviors—audible, behavioral, and expression—can be processed by the technology herein and feedback provided to a wearer of device 2. FIG. 7A illustrates a social situation such as a conversation. In FIG. 7A, individuals 702 and 704 could be close friends or business associates. Other social situations wherein the technology may be useful include romantic situations involving a one-on-one relationship between individuals. In addition, social situations may include more formal relationships, such as business interactions with subjects, small groups, and presentations to large groups. Interpretation of gestures and interactions between subjects or groups and the type of feedback can be biased based on the type of social scenario being evaluated. FIG. 7B illustrates an alternative scenario wherein a presenter 708 is making a presentation to a group of subjects who may or may not have devices 2. In the situation illustrated in FIG. 7B, the presenter 708 can utilize the present technology to ascertain feedback regarding the members of the audience to whom the presenter 708 is speaking. The device 2 can interpret changes in user posture, user gestures, audible input levels such as murmurs and or other factors to determine the emotional engagement of the audience. For example, slouched postures or wandering audience gaze might indicate a lack of interest or attention. This feedback is provided to the presenter 708 while the presenter during the presentation to allow the presenter to let the presenter know how the presenter is doing.

Figure 8:
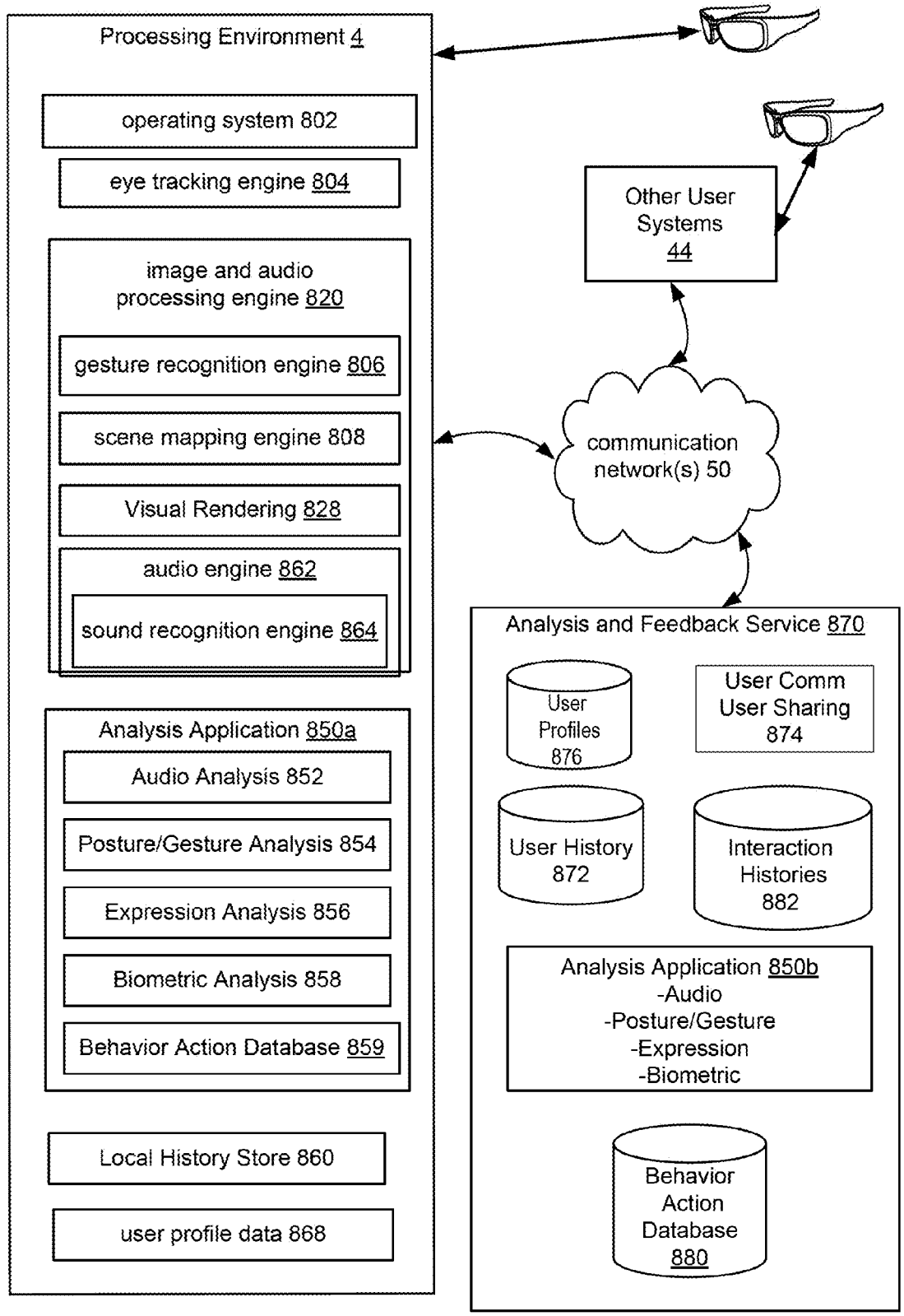
FIG. 8 is a depiction of functional components of a system including a processing environment and analysis and feedback service suitable for implementing the technology.

FIG. 8 illustrates the functional components of the processing environment including a local processing unit 4 and a remote, network connected processing environment implementing an analysis and feedback service 870. FIG. 8 is a block diagram of the system from a software perspective for providing an emotion detection system in see through head mounted mixed reality display. FIG. 8 illustrates a computing environment from a software perspective which may be implemented by personal computing apparatus in conjunction with one or more remote computing systems 870 in communication with one or more personal AV apparatus, or a combination of these. Network connectivity allows leveraging available computing resources including an analysis and feedback service 870.

As shown in the embodiment of FIG. 8, the software components of a processing unit 4 comprise an operating system 802, eye tracking engine 804, image and audio processing engine 820, and analysis application 850a, a local history store 860 and user profile data 868.

Operating system 802 provides the underlying structure to allow hardware elements in the processing unit 4 to interact with the higher level functions of the functional components shown in FIG. 8.

Eye tracking engine 804 tracks the wearer gaze with respect to movements of the eye relative to the device 2. Eye tracking engine 804 can identify the gaze direction or a point of gaze based on people position and eye movements and determine a command or request.

Image and audio processing engine 820 processes image data (e.g. video or image), depth and audio data received from one or more capture devices which may be available from the device. Image and depth information may come from outward facing sensors captured as the wearer moves his or her body.

Gesture recognition engine 806 can identify actions performed by a wearer indicating a control or command to an executing application 850a. The action may be performed by a body part of a wearer e.g. a hand or a finger, but also may include an eye blink sequence. In one embodiment, the gesture recognition engine 806 includes a collection of gesture filters, each comprising information concerning a gesture that may be performed by at least a part of a skeletal model. The gesture recognition engine 806 compares skeletal model and movements associated with it derived from the captured image added to gesture filters in a gesture library to identify when a wearer has performed one or more gestures. In some examples, matching an image data to image models of a wearer's hand or finger during a gesture may be used rather than skeletal tracking for recognizing gestures. Image and audio processing engine 820 processes image data depth and audio data received from one or more captured devices which might be available in a given location.

A 3D mapping of the display field of view of the augmented reality display device 2 can be determined by the scene mapping engine 808, based on captured image data and depth data for the display field of view. A depth map can represent the captured image data and depth data. A view dependent coordinate system may be used for mapping of the display field of view as how a collision between object appears to a wearer depends on the wearer's point of view. An example of the view dependent coordinate system is an X, Y, Z, coordinate system in which the Z-axis or depth axis extends orthogonally or as a normal from the front of a see through display device 2. At some examples, the image and depth data for the depth map are presented in the display field of view is received from cameras 113 on the front of display device 2. The display field of view may be determined remotely or using a set of environment data 854 which is previously provided based on a previous mapping using the scene mapping engine 808 or from environment data 880 in a mixed object reality service.

Visual rendering engine 828 renders elements in the wearer display, which can include instances of three dimensional holographic virtual objects, two dimensional images, colors and other information within the display of a display device 2. Visual rendering engine 828 works in conjunction with application 850a to render elements in a display.

An audio recognition and rendering engine 862 interprets input from audio inputs such as microphone 110.

Application 850a provides a wearer with feedback concerning interactions with subjects or groups of people within the field of view of the wearer. Application 850a includes audio analysis component 852, posture and gesture analysis component 854, expression analysis 856, biometric input analysis 858 and local history store 860. Audio analysis component 852 receives input from sensors on device 2 including microphone 110 for use in determining emotional states of parties in the wearer field of view. Audio recognition and rendering engine 862 provides linguistic analysis of audio input as described herein. In one aspect, audio analysis is provided by application 850a using data provided by sensors on device 2. In other embodiments, analysis is performed in conjunction with application 850b running in a network connected analysis and feedback service 870.

Each of the audio analysis component 852, posture/gesture analysis component 854, expression analysis component 856, and biometric analysis component 858 cooperate to provide an indication of an emotional state of a subject who may be within the field of view of a wearer of a see through head mounted display 2. The accuracy of the determination of an emotional state of a subject interacting with or observed by a wearer may depend on the input factors analyzed and the processing power of processing unit 4. In addition, a local history of detected interactions referenced by subject may be retained in a local history store 860.

Each of the analysis components matches recognized inputs (visual or audible) to an interpretation of that input relative to a behavior action database 859. Each of the individual components 852, 854, 856, and 858 isolates and recognizes a behavior which can be compared to a corresponding emotional state in database 859. As each interaction will have multiple recognized behaviors occurring simultaneously, the analysis application 850a weighs any combination of inputs and associated behaviors at a given time and derives a conclusion about an emotional state to report feedback on given the inputs. A local history store 860 records each interpretation for the current interaction, and in one embodiment, past interactions with identified subjects. The local history of an interaction can be included in determining an emotional state of current input behaviors.

Determination of emotional states can include analysis of audible and visual inputs. Audible inputs can include expression, speech and word analysis, word choice and syntactic framing of utterances, and speech pace, rhythm, and pitch contour all provide indications of an observed subject's emotional state. In addition, a subject's gestures, expressions, and body language all reflect emotional state.

User profile data 868 may include information on the wearer, including past detected emotional states of the wearer, other subjects with whom the wearer may have chosen to share emotional determinations made by a device 2 worn by the wearer, and past histories of subjects with whom the wearer has interacted.

Wearer profile data 858 includes wearer specific information such as wearer specific objects, and preferences associated with one or more wearers of the device.

Analysis and feedback service 870 similarly includes an analysis application 850b and a behavior action database 880. In one embodiment, the service 870 can provide additional processing capability to any processing unit 4 to allow a greater number of inputs and additional input factors to be considered in a behavioral analysis.

Service 870 includes a user communication and sharing component 874 allowing one or more devices 2 to connect to the service via a network 50. Service 870 can store a plurality of user profiles 876, user history 872 and interaction histories 882 for wearers who avail themselves of the service.

A user sharing and communication component 874 may also allow users to share interaction interpretations made by their device with other users, or provide additional input (such as for example biometric data) to other devices for interpretation. As discussed below, such sharing is based on use of authentication and wearer-defined permissions indicating the specific types of input and information which may be shared and with whom such sharing may occur. Such sharing may be managed by the communication and sharing component 874 or in a peer to peer setting by a sharing component on each processing unit 4.

FIG. 9 is a flow chart illustrating a method for providing emotional feedback for subjects within the field of view of a wearer of a see through head mounted display device, such as that illustrated in FIGS. 1 through 6. It should be understood that in this context, the term "field of view" refers not only to a visual area which is viewable by the wearer of a device 2, but also an audible detection area which can be perceived by the sensors of the device 2.

Method 900 may be performed by an application 850a, application 850b or a combination of the applications. Alternatively, the analysis step 916 discussed below may be supplemented or performed by the service 870.

Initially, at step 902, a wearer may be provided with the opportunity to select a social situation or scenario that the wearer wishes to acquire feedback about. Two exemplary choices of scenarios may include a social situation or a business situation. In the analysis of emotional feedback from subjects within the wearer's field of view, actions may mean different things on the part of the subject. For example, if a subject plays with her hair in a social situation, such as a date, this behavior may indicate friendliness or interest. However, the same behavior in a business situation may indicate boredom. If a wearer opts to select a scenario at 902, then the technology alters the interpretation behaviors at 903 which assigned to the audible and visual actions it perceives in a particular scenario. This can indicate a bias toward different types of results for different types of actions, such as the twirling of one's hair as discussed above. If the wearer does not select a particular scenario at 902, then a default set of baseline interactions is used at 904.

Each of the baseline interactions and the specific social interactions are a set of interpretive responses to audio and visual inputs as characterized by the components of the analysis application 850*a*/850*b*.

At 906, the wearer's location, orientation, and gaze are determined. The location may be a geographical location, or a known location such as the wearer's home or the wearer's place of business. The factors such as the wearer's location can influence the determination of the types of interactions which are being engaged in, as well as the bias in determining whether a particular emotion is being expressed or not. The initial orientation and gaze allow the determination of which other subjects might be within the wearer's field of view at 908. At 908, a determination is made of which parties in the wearer's view should be analyzed. In one embodiment, a wearer may select feedback for specifically identified subjects, while in another embodiment an automatic determination of subjects is made. A manual determination can include specifically identifying known subjects for whom the wearer has interacted in the past, and retrieving the subject's history from a database of stored interactions. This can improve the detection of the emotional feedback provided by the technology. In alternative scenarios, subjects are identified in a manner to distinguish subject from other subjects, so that feedback for each of the subjects being tracked can be maintained. Where a group of subjects is within the wearer's field of view, a wearer may select to receive feedback from only one subject, the group, or a subset of the group within the wearer's field of view.

It should be understood that variation in subjects can be selected by the wearer's gaze. As noted above, a display device 2 includes the ability to detect the target of a wearer's gaze which can include the subject with whom a wearer is focused. Analysis of subjects can be selected by wearer gaze and can changed based on the gaze of a wearer.

In one embodiment, the storage of user interactions is not a strict recording of image and audio data, but rather interaction semantics relating user actions to detected responses, without storing specifics. For example, a history might include a reference to a particular word or wearer gesture that consistently generates a particular gesture or response by the subject. For example, whenever the wearer mentions the word "marriage", the subject is detected to be looking down.

In one embodiment, this information can be collected and presented to the user via in interface (in device 2 or another interface) allowing the wearer to study the interactions and learn from them.

Steps 912 through 920 represent a loop where—for inputs received regarding the wearer's orientation, gaze, audio input and location at 912 and for each analyzed wearer at 914—an emotional determination analysis is performed at 916 to allow the system to provide feedback to the wearer of the device. Once the determination is made at 916, feedback is provided at 918 and, optionally, in 920, the context and feedback of the interaction can be stored. Feedback is provided continuously as the wearer participates in various interactions with subjects within the field of view. Inputs from the device 2 are received at 912 continuously. Steps 914-918 may be performed continuously, at intervals determined by changes in the input, or at timed intervals. For example, interaction input may determine only when major changes in an analyzed subject's emotional state occur, and provide feedback only on such major changes.

Figure 10B:
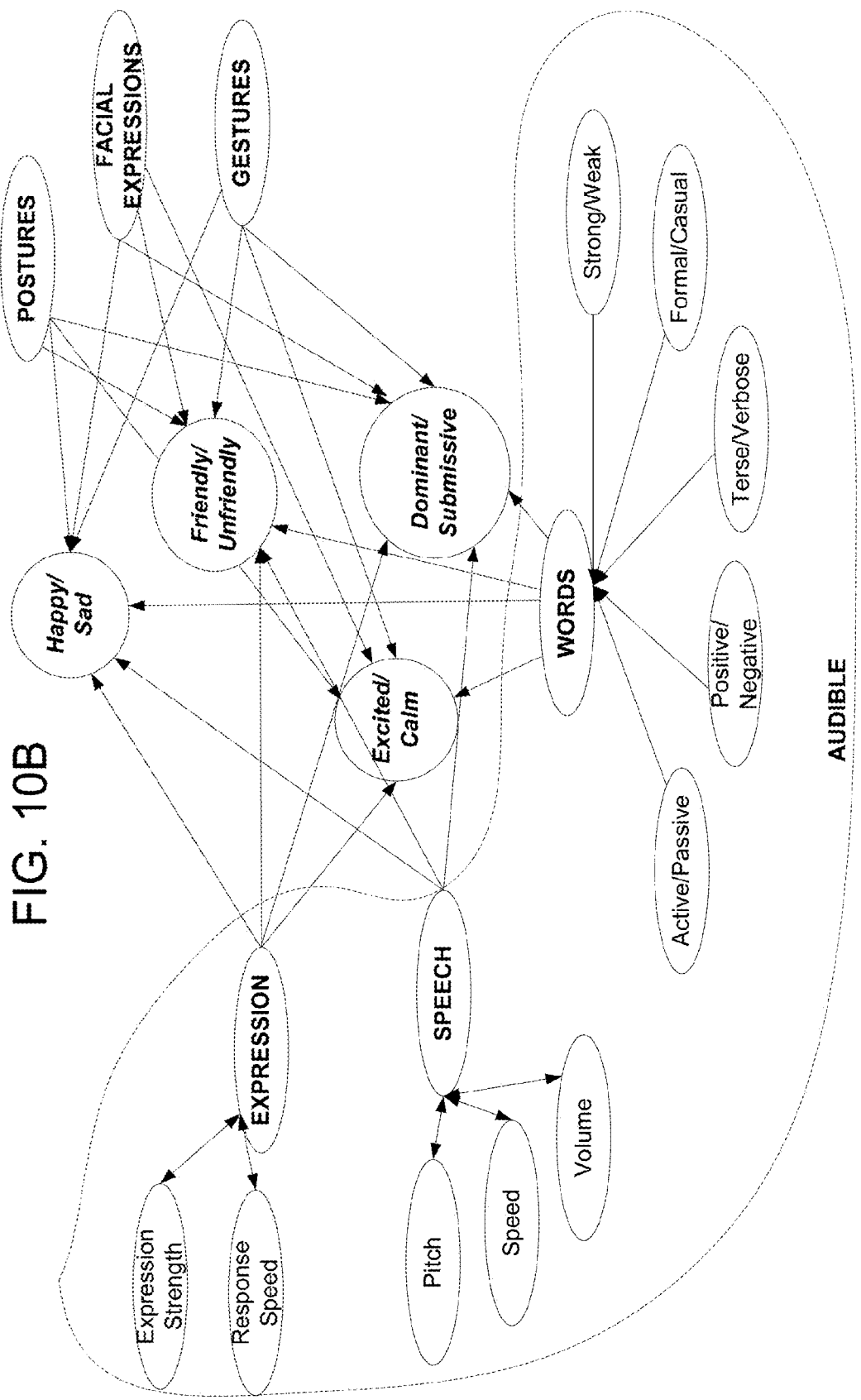
FIG. 10B is a graph illustrating a Bayesian network of elements used in the analysis of FIG. 10A.

FIG. 10A illustrates one embodiment of the analysis step 916 of FIG. 9. In FIG. 10A, at 1012, for each type of data input—image data, audio data, depth data—which may be provided by the device 2, such input is added to the analysis engine (FIG. 10B) and matches between the input and speech patterns, word patterns, gestures, postures and/or expressions for an subject or group being interpreted at 1015. A collection of matched behaviors is evaluated at 1016 to conclude an emotional state. Optionally, at 1018, a confidence weight can be assigned. Where a limited number of inputs or matches occur relative to possible conclusions at 1016, an indication of the strength of the conclusion can be assigned at 1018 and incorporated into the feedback provided. Appropriate feedback is determined at 1020. Various types of feedback are disclosed herein, some of which may be selected by the wearer based on type, or a simple warning that the wearer may be performing an action or the response generated by an subject within the wearer's field of view is a negative one, coloring the wearer's display may be appropriate.

FIG. 10B represents a model of dependencies which may be used to determine various emotional states. Emotion generally means a short term variation in an internal mental state, including both physical responses and cognitive responses. In the model of FIG. 10B, current emotional states are characterized by input value in a Bayesian network model. Each type of emotion—happy/sad, friendly/unfriendly, excited/calm, dominant/submissive—are derivable from observable visual and audible input. Each type of input—audible, gestures, expressions and postures—can be resolved from device audio and image input data.

Emotional states are communicated through a variety of nonverbal and verbal behaviors. While people are generally sensitive to signals produced by others, some people do not pick upon these signals. The range of linguistic and nonlinguistic behaviors that transmit information is exceedingly large. One's emotional arousal, whether one is excited or calm, affects a number of easily observed behaviors including speech speed and amplitude, the size and speed of gestures, and aspects of facial expression, posture and gestures. One method of communicating emotional state is by choosing among semantically equivalent but emotionally diverse paraphrases. For example, simply saying "yes" can be stated as "yes", "yeah", "I think so", "absolutely", "I guess so", or "for sure." Each of these particular types of paraphrases can be related to a particular emotional state illustrated in FIG. 10B.

In FIG. 10B, resolved data types for the audible input realm are expanded and illustrated. It should be recognized that each of the postures, facial expressions and gestures may likewise have additional inputs. In the audible input realm 1050, behaviors can include the type of expression used, the subject' speech, and the subject's specific words. Expressions can be evaluated based on the strength of the expression, and a subject's response speed to an utterance of the subject. Within a speech behavior, the subject's pitch change, speed of speech, and volume can all be behavioral indicators. The words used by a subject can include strong or weak words, formal or casual words, terse or verbose language, positive or negative words, or active or passive words. While the audible realm 1050 is illustrated, each of the other behavioral classes such as postures, facial expressions, and gestures likewise have a number of behavioral inputs. It should be noted that the emotions illustrated in FIG. 10B are merely illustrative and additional types of inputs and variables may be utilized. The understanding of emotion personality is the focus of extensive psychology literature. The model of FIG. 10B may be varied to be more simplistic or more detailed depending on the goal of the technology in particular instances. The model of FIG. 10B integrates information from a variety of observable linguistic and nonlinguistic behaviors derived from the device 2. Various classes of these effects are shown.

Figure 11:
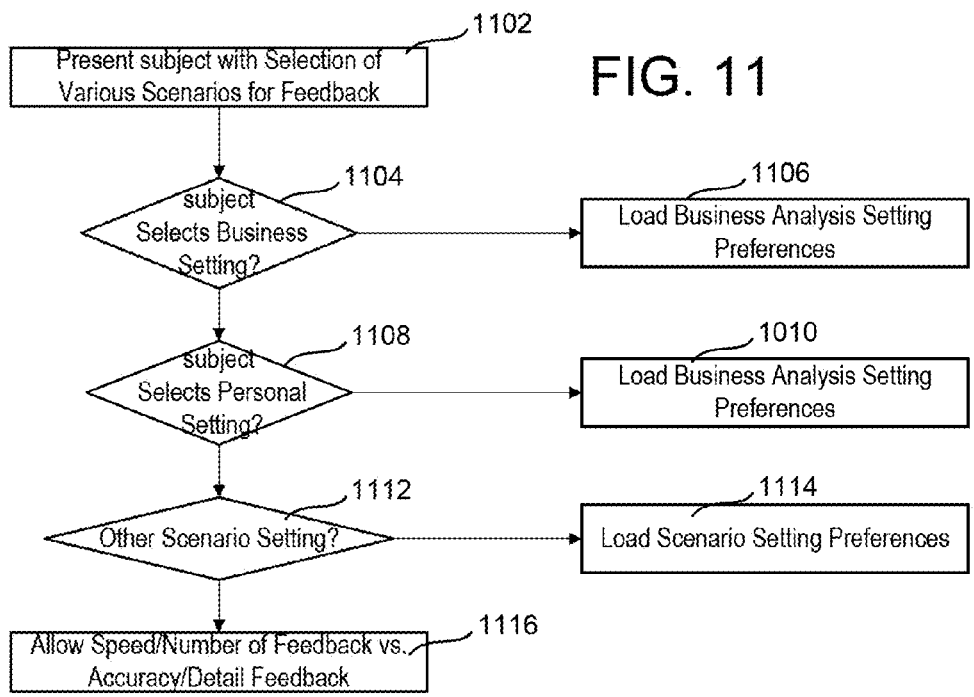
FIG. 11 is a flow chart representing step 902 in FIG. 9.

FIG. 11 is a method for presenting a wearer with a selection of one or more various scenarios for a feedback type based on a particular social situation that the wearer is engaged in.

At 1102, a wearer is presented with a selection of various scenarios for feedback. The scenarios may include "social situation" 1104, "business situation" 1108 or specific situations 1112 which may be for example "party", "wedding", "meeting", "presentation" and the like. For each type of setting, emotional interaction biases toward evaluation of particular behaviors responsive to the inputs are applied 1106, 1110 and 1114. If no specific scenario is selected, the wearer may be presented with an interface to allow the wearer to select a tradeoff between providing greater speed or frequency of feedback versus the accuracy and detail of feedback at 1116. Given the number of different behaviors that are interpreted by the emotion detection application, a tradeoff can be made between providing feedback on a more limited set of behaviors but with a quicker response, versus processing a greater set of inputs to provide a more detailed response. The response at step 1116 can also enable reference to the analysis and feedback service 870 by allowing more processing to occur by application 850B rather than at the local processing on application 850A.

Figure 12:
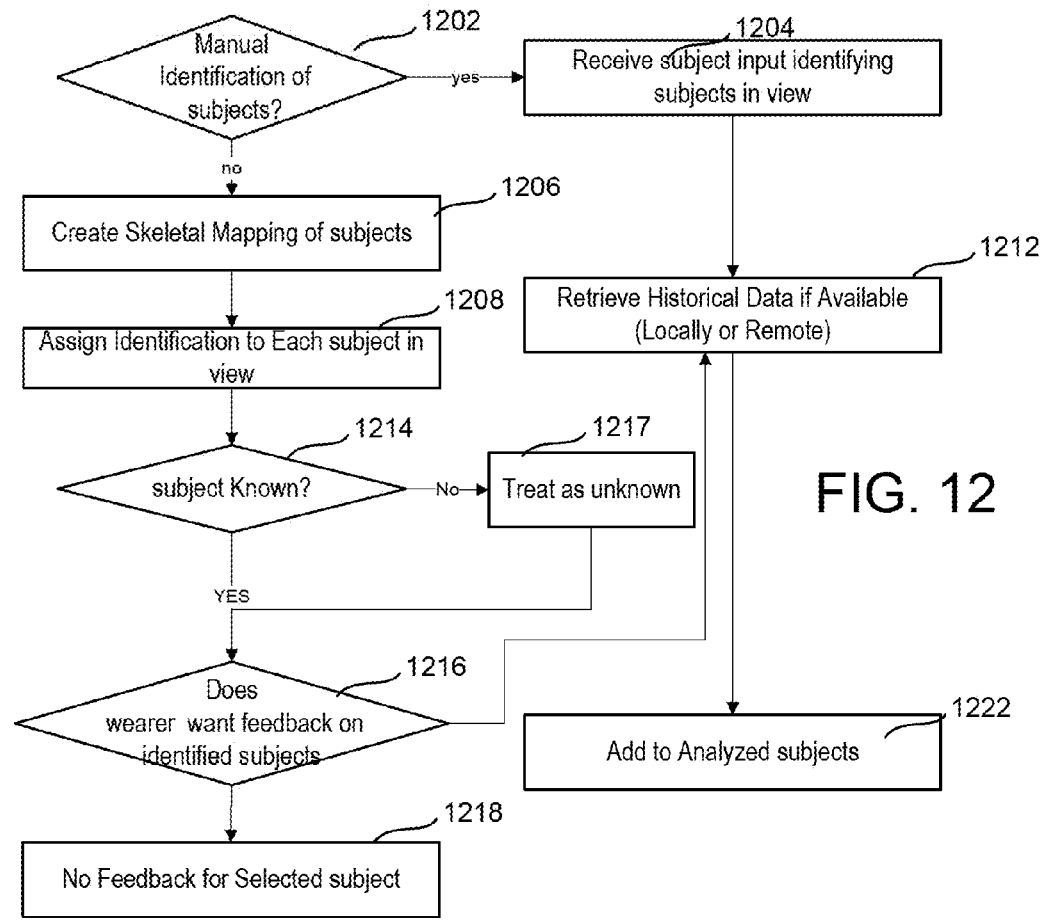
FIG. 12 is a flow chart representing determination of subjects in a user field of view to analyze which may be one embodiment of step 908 in FIG. 9.

FIG. 12 illustrates one embodiment for determining of which subjects to analyze, which may be one embodiment of step 908 in FIG. 9. At 1202, a wearer may be presented with an interface to allow manual selection of subjects for analysis. If the wearer chooses to manually select and identify wearers within the wearer's field of view, then wearer input is received at 1204. Input can take the form of presenting the wearer with a selection or highlighting of various persons within the display field of the device 2, and allowing the wearer to select from a menu of possible options and how to identify the particular wearer. This can be made in reference to a contact list stored in user profile data 868 on the processing unit 4, historical data based on a frequency in the number of subjects that a wearer has interacted with, or other input means. Once input is received at 1204, historical data for the identified subject is retrieved if available at 1212. If the wearer has interacted with a particular party previously, these interactions can be useful in determining whether or not the emotional feedback provided to the wearer is accurate. For example, a data set on a particular subject may determine that this particular subject generally cries quite frequently and that the expressions associated with crying do not necessarily mean that the subject is sad. If crying expressions are detected along with audible input indicating crying, this historical knowledge can be used to more accurately determine whether the crying is an expression of joy or sorrow. Once historical data is retrieved if available the subjects are added to the list of analyzed subjects at 1222. If the wearer chooses not to manually identify other parties, then a skeletal mapping of subjects within the wearer's field of view is made at 1206 and identification assigned to each wearer in the field of view at 1208. Identification at 1208 may be as basic as simply discerning between different subjects based on an associated skeletal model with the subject, or may seek to identify the subject from a set of known subjects which are stored in the analysis and feedback service 870 or in the local history store 860 in the processing unit 4. If the wearer is determined to be a known previous wearer at 1214, and, at 1216, the wearer has decided to request feedback on the party, then again, historical data will be retrieved if available at 1212 and the subject added to the list of analyzed subjects at 1222. If the subject is not known, then the subject will be treated as unknown at 1216 and the wearer will be presented with a choice of whether or not to provide feedback on the wearer at 1216. It should be recognized that the step of providing the wearer the option to select whether feedback is available for a particularly identified party in the wearer's field of view is optional. If the wearer does not want feedback on any identified subject, the selected subject is removed from analysis by the analysis engine.

Figure 13:
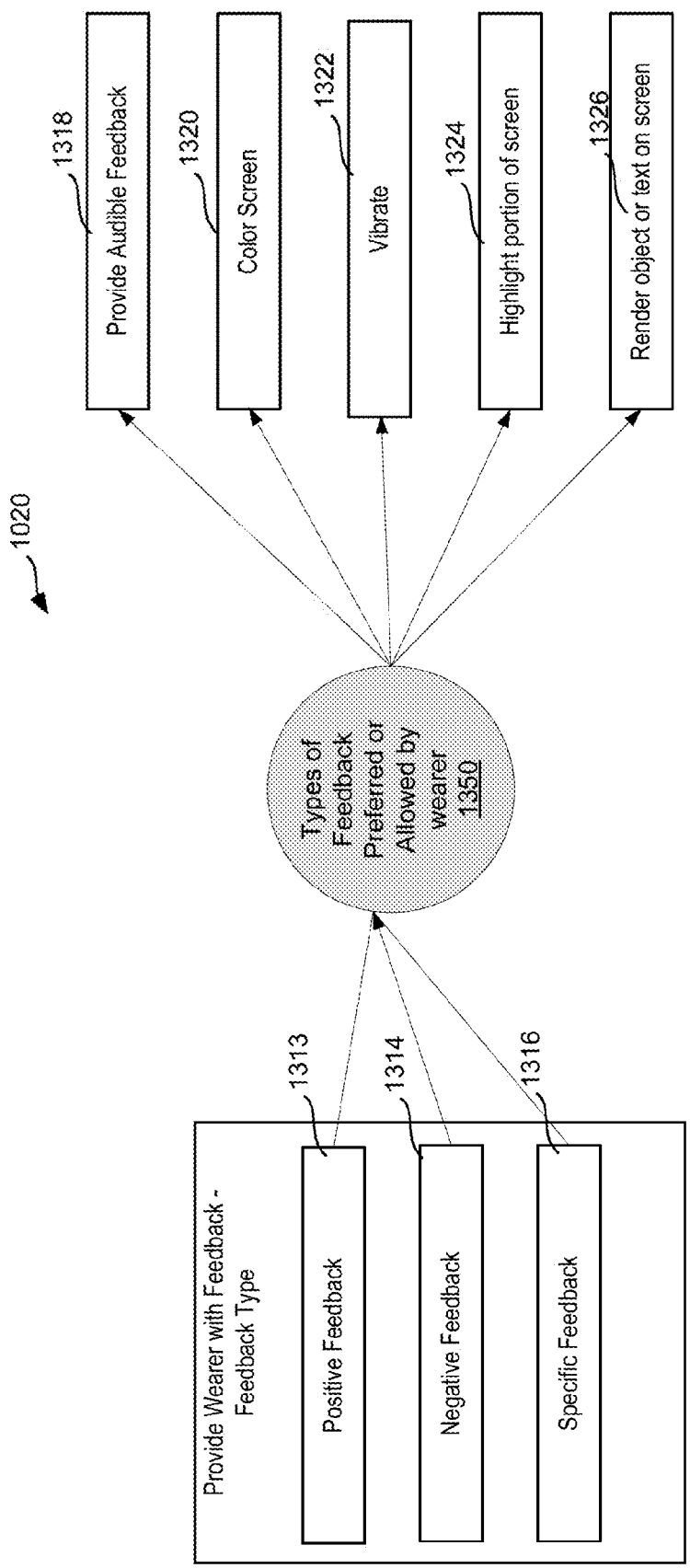
FIG. 13 illustrates a method for user selection of feedback types, which may comprise one way of providing a wear with emotional feedback in step 918 of FIG. 9.

FIG. 13 illustrates how different types of feedback may be presented based on the type of the feedback to be presented and selections made by a wearer of the device. At 1313, 1314 and 1316, a determination is made as to whether positive feedback, negative feedback or specific feedback on the particular emotion detected is to be presented to the wearer. The right side of the figure illustrates different types of feedback and is a non-exhaustive list of those types of feedback which can be presented to a wearer of a device 2. These include providing audible feedback 1318, tinting the screen through which the wearer views real objects and subjects at 1320, vibrating the device, highlighting a portion of the screen with feedback 1320, or rendering an object or text on the screen at 1322. For each different type of feedback, positive 1313, negative 1314, or specific 1316, a filter 1350 will be consulted to determine which types of feedback a wearer may have previously selected to view or which a wearer prefers based on a specific selection or historical information from the wearer. Once the wearer's specific preferences are accounted for by filter 1350, any of the different types of feedback 1318, 1320, 1322, 1324 or 1326 can be utilized to present specific positive and negative feedback to a wearer. Examples of different types of feedback are provided below.

Figure 14:
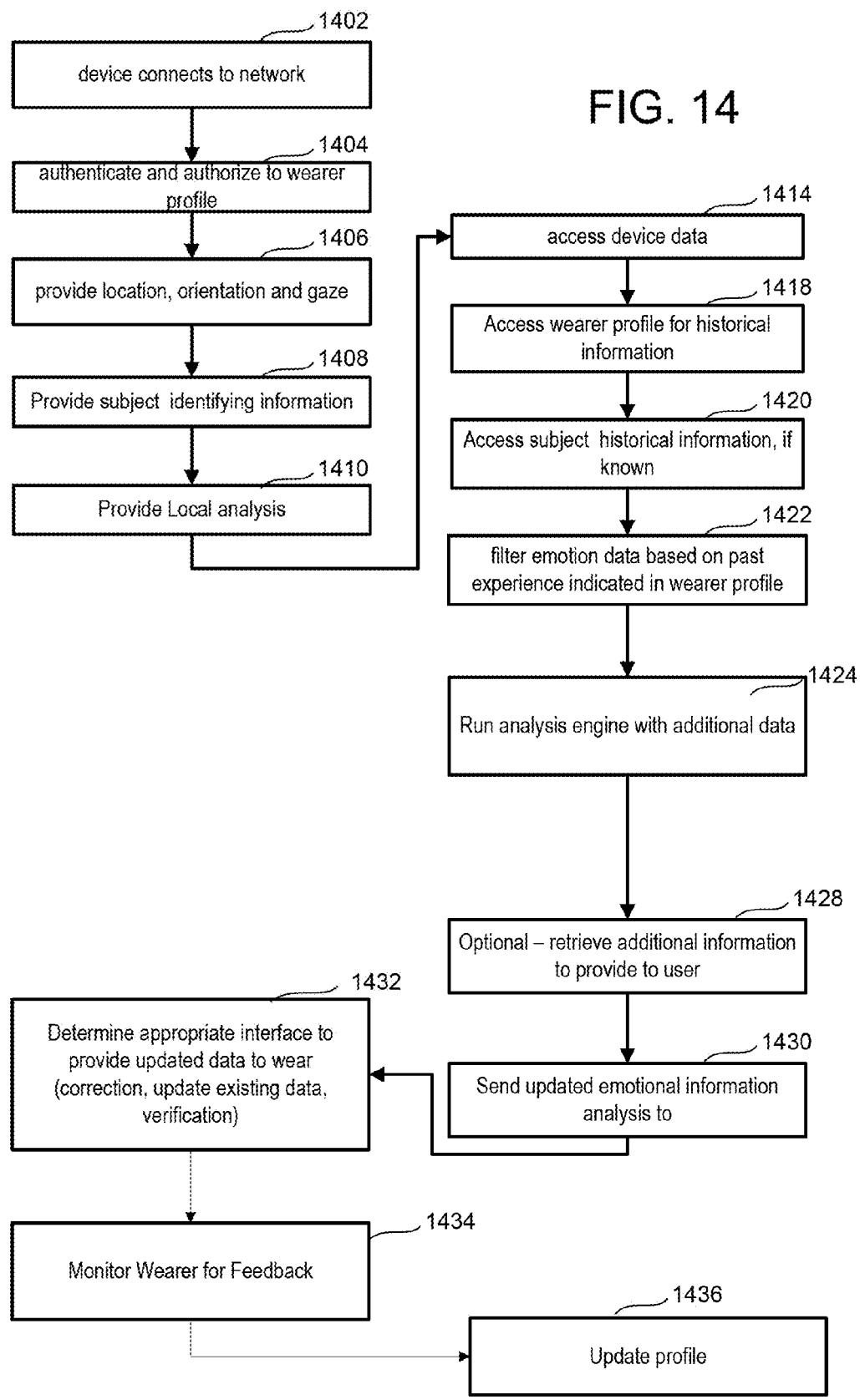
FIG. 14 is a flow chart illustrating the analysis step 916 of FIG. 9 when both a local processing device and a network connected service are utilized to perform the analysis.

FIG. 14 is a flow chart illustrating a method for utilizing a service 870 to process emotional interactions in conjunction with the present technology. In FIG. 14, the left side of the figure represent operations occurring on a local processing device, local being proximate to the wearer, such as processing unit 4, while the right side steps illustrate operations which may be occurring on a service such as service 870.

At 1402, a see though head mounted display device may connect to the network 50 illustrated in FIG. 8 and at 1404 authenticate and authorize the wearer to an associated wearer profile on the service 870 at 1404. Location, orientation, gaze, and audible information will be provided to the service 870 at 1406 and party identification information for those subjects within the field of view of the wearer will be presented at 1408. In addition, and optionally, a local analysis generated by application 850A may be provided to the service 870 at step 1410.

At 1414, the service accesses device data received in steps 1406, 1406 and 1408, and accesses wearer profile for historical information at 1418. At 1420, profile information for those subjects within the wearer's field of view is accessed at 1420 if such information is available. At 1422, emotional data based on past experience with individual wearers between the wearer of the device and such subject is filtered as indicated in the wearer profile. At 1424, the analysis (application 850B) on the service can be run with additional information known on the by the service. Optionally, at 1428, additional information can be retrieved from the wearer and looped through the analysis engine at 1424. At 1430, updated emotional information analyzed by the service 870 is forwarded to the local processing device and at 1432 the appropriate interface to provide the updated data to the wearer is presented. In this context, at step 1432, this can include updating an originally analyzed situation with new information. For example, if a local analysis is determined that crying means an subject within the wearer's field of view is sad, but the service has determined that the subject regularly cries and therefore crying, given all the other input factors, does not mean that the wearer is sad, this can be overridden and feedback provided to the wearer in one of any of the contexts set forth in FIG. 13. At 1434, feedback from the wearer on the accuracy of the analysis can be provided, and at 1436, the profile of the wearer updated for use in future emotional detection scenarios.

Figure 16A:
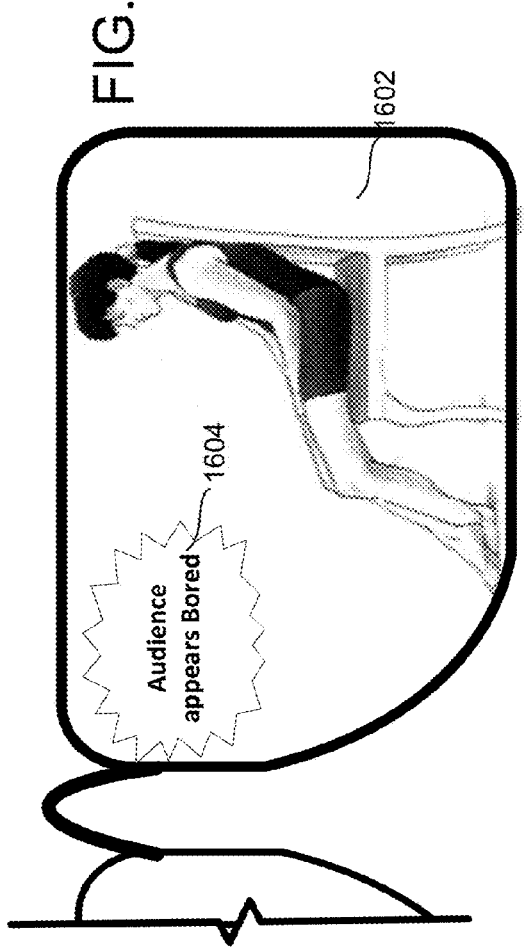
Figure 17A:
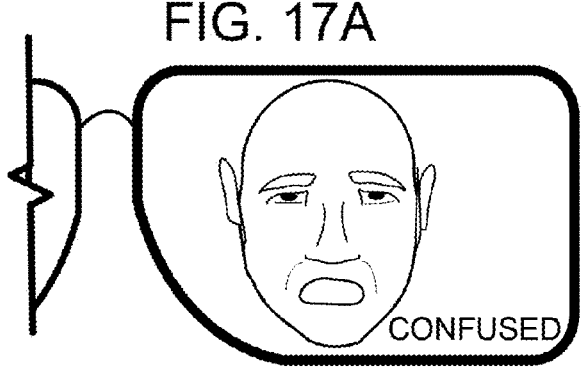
FIG. 17A-17F illustrate various types of expressions and visual feedback which may be provided to the wearer of a see through head mounted display device.
Figure 17B:
Figure 17C:
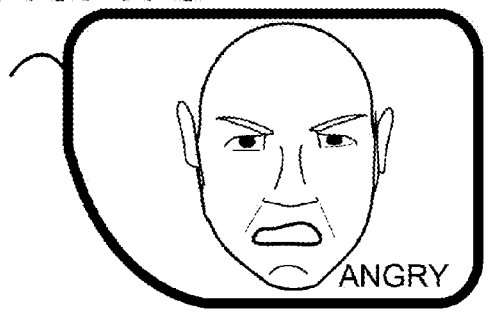
Figure 17D:
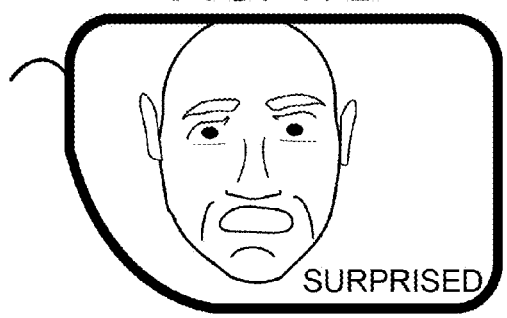
Figure 17E:
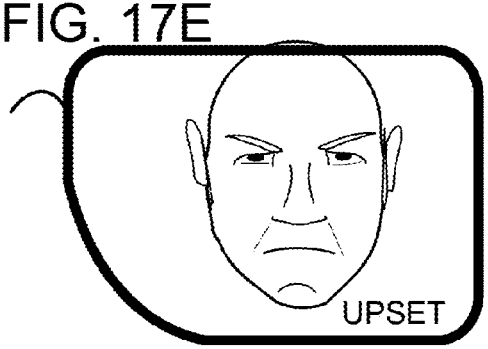
Figure 17F:
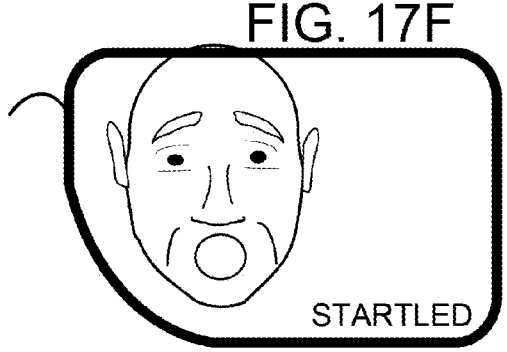

FIGS. 15A and 15B illustrate one manner of providing visual feedback to a wearer regarding the emotional interaction with a wearer. In FIG. 15A, a wearer of 1529 and a subject 1528 are engaged in a conversation. Subject 1528 utters the word "interesting" which, given the additional input factors results in a display 1510 of a yellow color in the view screen of the wearer 1529. The color indicator 1510 can be a highlighted portion of the corner of the wearer's display as illustrated in FIG. 15A, or as illustrated in FIG. 15B can represent highlighting the entire lens in the wearer's field of view. FIG. 15B represents an alternative scenario wherein the utterance of the term "interesting" is coupled with a facial expression which tends to indicate that the speaker is not happy. This can result in the flash of a red color as opposed to a yellow color since the determination has been made by the application engine that the term "interesting" in conjunction with the facial expression of the speaker means that the speaker is annoyed. In FIG. 16A, the posture of the subject 1602 within the field of view of the wearer is likely to indicate that the wearer is bored. Hence, specific information stating that the system has determined that the wearer in this case a member of the presentation audience is bored can appear at 1604. Similarly, in a situation where the audience is wrapped with attention, at 1606 the posture of the subject can be indicative that the presentation being made by a wearer is good and positive feedback in the form of a "thumbs up" signal provided at 1610.

FIGS. 17A through 17F illustrate various facial expressions in different types of feedback which can be provided based on each of the different facial expressions. In FIGS. 17A through 17F, each expression may be characterized by an emotional state which is displayed with specific feedback—the system's interpretation of the expression (and other input factors)—that the system has determined the subject to be exhibiting. Upon empirical review, it will be noted that the mere expression in each of the figures may mean one or more emotions.

FIG. 18 illustrates an alternative embodiment of the technology wherein data shared between wearers of see through head mounted displays having emotion detection capability is provided to other wearers to increase the accuracy of the device.

In FIG. 18, like reference numbers represent like steps to those set forth in FIG. 9. In FIG. 18, an additional sharing step 1810 and an import shared data step 1815 are illustrated. Data may be provided by a wearer at 1810 to provide additional data from a wearer's own device to another wearer. The data may be data retrieved by the sharing user's device sensors, or evaluation data derived by an analysis engine (850a/850b) operating on behalf of the sharing wearer on a subject, or biometric data adding to the interpretation data available to the analysis engine of the user with whom the information is shared. Sharing data can include the analysis provided by the wearer's engine of the wearer's own state, or specific feedback of a subject provided by the wearer in a given context. For example, the wearer's own device may present the wearer with an interface allowing the wearer to receive feedback on the determination being made by the wearer's device. For example, if the wearer is crying, the device can determine that the wearer is sad based on the fact that the wearer is crying. However, the wearer may be crying because the wearer is happy and may be able to override the determination by reference to a specific gesture or wearer interface command. The sharing data can be output to a selected number of other wearers with whom the wearer has decided to share information. During the analysis step at 1815, import of shared data from the wearer's shared set can be used to bias the analysis engine at 1012 or, provide specific data indicating the emotional state specified by the sharing subject.

Figure 19:
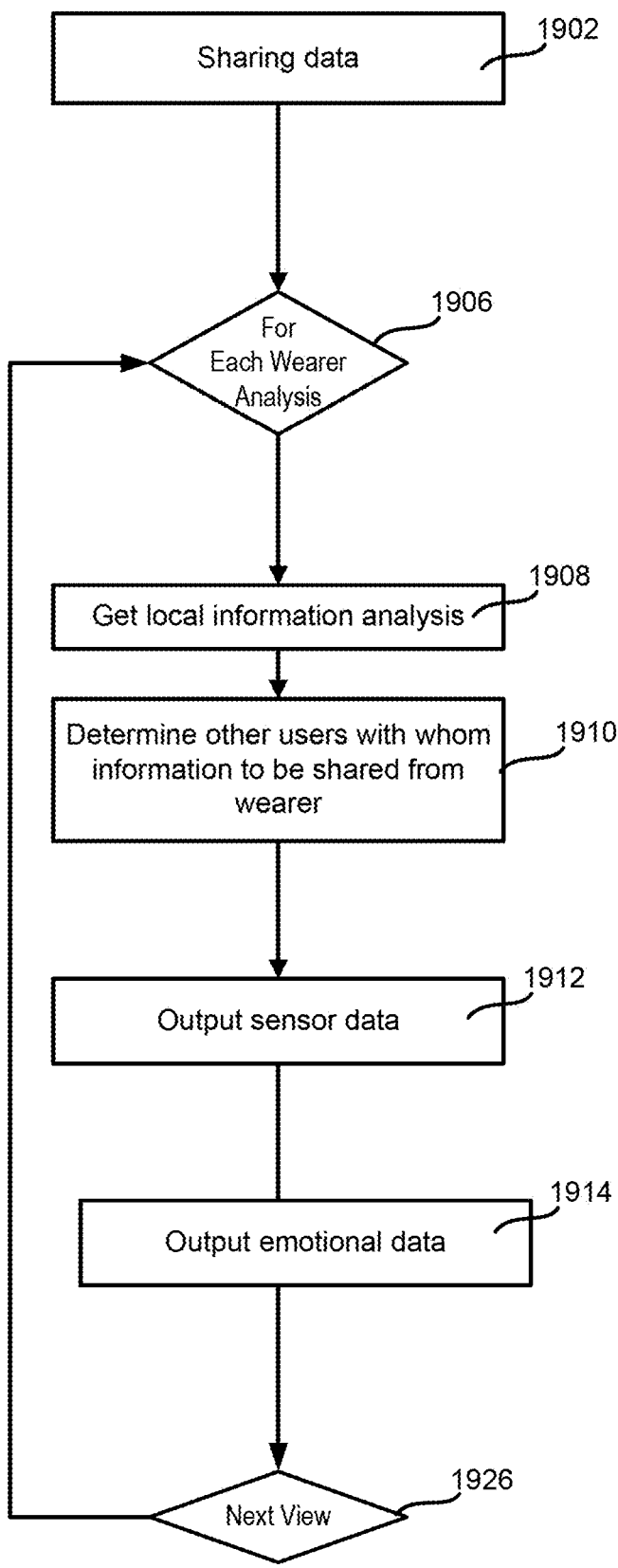
FIG. 19 illustrates the step of providing sharing data which may be one embodiment of step 1811 in FIG. 18.

A method for sharing data is illustrated in FIG. 19. At 1902, for each wearer analysis at 1906, a local information analysis at 1908 is retrieved and a determination made at 1910 of additional wearers of devices having emotional detection capability with whom the sharing subject has decided to share information is made. At 1912, sensor data from the sharing wearer's device may be provided and at 1914 specific emotional feedback presented manually by the sharing subject can be output before a next view is presented at 1926.

Figure 20:
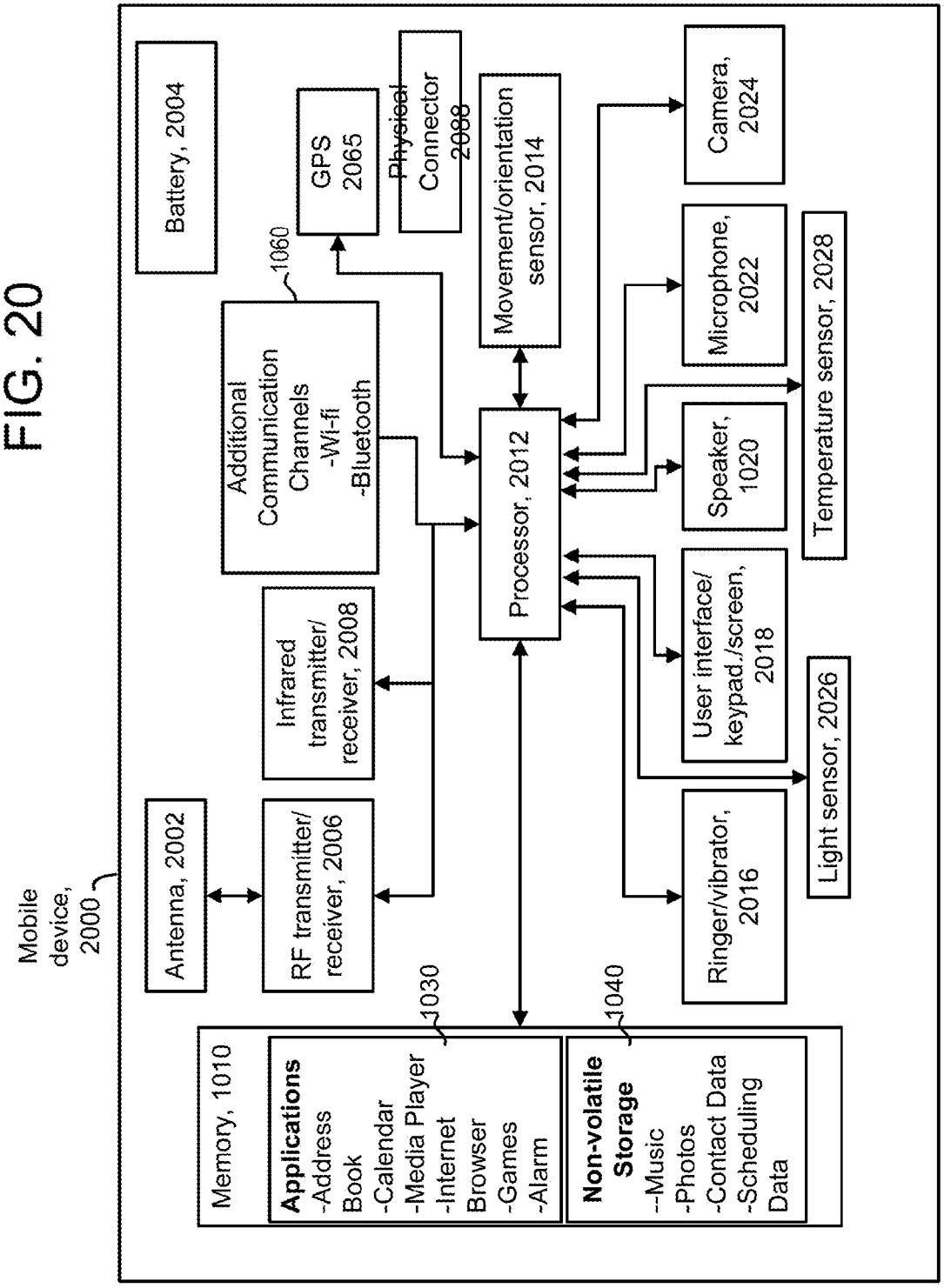
FIG. 20 is a block diagram of an exemplary processing device.

FIG. 20 is a block diagram of an exemplary mobile device which may operate in embodiments of the technology described herein (e.g. processing unit 4). Exemplary electronic circuitry of a typical mobile phone is depicted. The device 2000 includes one or more microprocessors 2012, and memory 2010 (e.g., non-volatile memory such as ROM and volatile memory such as RAM) which stores processor-readable code which is executed by one or more processors of the control processor 2012 to implement the functionality described herein.

Mobile device 2000 may include, for example, processors 2012, memory 2050 including applications and non-volatile storage. The processor 2012 can implement communications, as well as any number of applications, including the interaction applications discussed herein. Memory 2050 can be any variety of memory storage media types, including non-volatile and volatile memory. A device operating system handles the different operations of the mobile device 2000 and may contain wearer interfaces for operations, such as placing and receiving phone calls, text messaging, checking voicemail, and the like. The applications 2030 can be any assortment of programs, such as a camera application for photos and/or videos, an address book, a calendar application, a media player, an Internet browser, games, other multimedia applications, an alarm application, other third party applications, the interaction application discussed herein, and the like. The non-volatile storage component 2040 in memory 2010 contains data such as web caches, music, photos, contact data, scheduling data, and other files.

The processor 2012 also communicates with RF transmit/receive circuitry 2006 which in turn is coupled to an antenna 2002, with an infrared transmitted/receiver 2008, with any additional communication channels 2060 like Wi-Fi or Bluetooth, and with a movement/orientation sensor 2014 such as an accelerometer. Accelerometers have been incorporated into mobile devices to enable such applications as intelligent wearer interfaces that let wearers input commands through gestures, indoor GPS functionality which calculates the movement and direction of the device after contact is broken with a GPS satellite, and to detect the orientation of the device and automatically change the display from portrait to landscape when the phone is rotated. An accelerometer can be provided, e.g., by a micro-electromechanical system (MEMS) which is a tiny mechanical device (of micrometer dimensions) built onto a semiconductor chip. Acceleration direction, as well as orientation, vibration and shock can be sensed. The processor 2012 further communicates with a ringer/vibrator 2016, a wearer interface keypad/screen, biometric sensor system 2018, a speaker 2020, a microphone 2022, a camera 2024, a light sensor 2026 and a temperature sensor 2028.

The processor 2012 controls transmission and reception of wireless signals. During a transmission mode, the processor 2012 provides a voice signal from microphone 2022, or other data signal, to the RF transmit/receive circuitry 2006. The transmit/receive circuitry 2006 transmits the signal to a remote station (e.g., a fixed station, operator, other cellular phones, etc.) for communication through the antenna 2002. The ringer/vibrator 2016 is used to signal an incoming call, text message, calendar reminder, alarm clock reminder, or other notification to the wearer. During a receiving mode, the transmit/receive circuitry 2006 receives a voice or other data signal from a remote station through the antenna 2002. A received voice signal is provided to the speaker 2020 while other received data signals are also processed appropriately.

Additionally, a physical connector 2088 can be used to connect the mobile device 2000 to an external power source, such as an AC adapter or powered docking station. The physical connector 2088 can also be used as a data connection to a computing device. The data connection allows for operations such as synchronizing mobile device data with the computing data on another device.

A GPS transceiver 2065 utilizing satellite-based radio navigation to relay the position of the wearer applications is enabled for such service.

Figure 21:
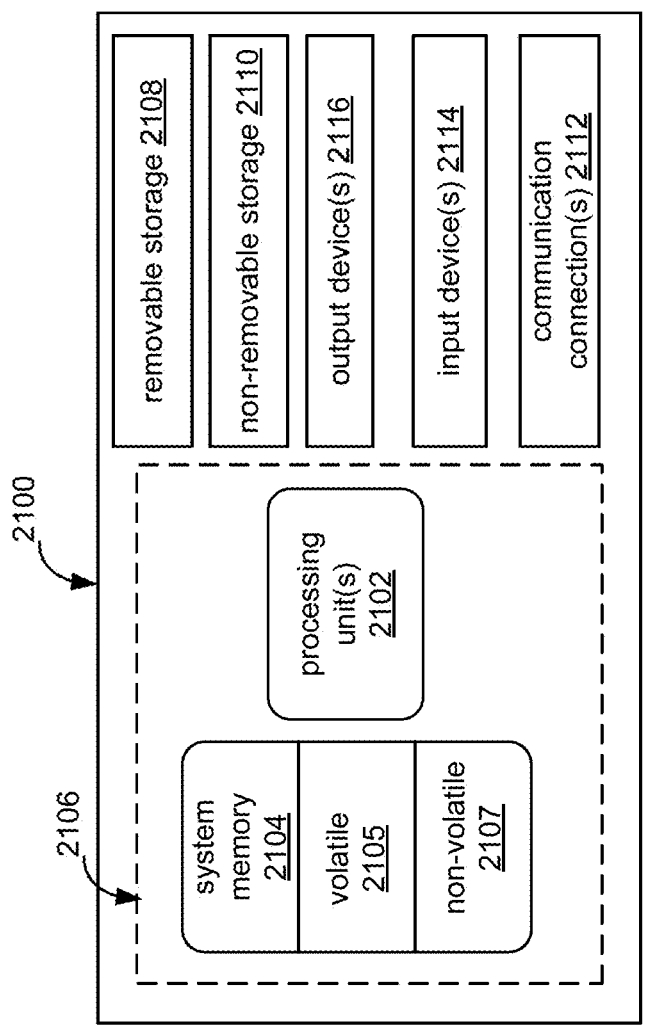
FIG. 21 is a block diagram of another exemplary processing device.

FIG. 21 is a block diagram of one embodiment of a computing system that can be used to implement a network accessible computing system or a companion processing module. FIG. 21 is a block diagram of one embodiment of a computing system that can be used to implement one or more network accessible computing systems 12 or a processing unit 4 which may host at least some of the software components of computing environment depicted in FIG. 12. With reference to FIG. 16, an exemplary system includes a computing device, such as computing device 2100. In its most basic configuration, computing device 2100 typically includes one or more processing units 2102 including one or more central processing units (CPU) and one or more graphics processing units (GPU). Computing device 2100 also includes memory 2104. Depending on the exact configuration and type of computing device, memory 2104 may include volatile memory 2105 (such as RAM), non-volatile memory 2107 (such as ROM, flash memory, etc.) or some combination of the two. This most basic configuration is illustrated in FIG. 21 by dashed line 2106. Additionally, device 2100 may also have additional features/functionality. For example, device 2100 may also include additional storage (removable and/or non-removable) including, but not limited to, magnetic or optical disks or tape. Such additional storage is illustrated in FIG. 16 by removable storage 2108 and non-removable storage 2110.

Device 2100 may also contain communications connection(s) 2112 such as one or more network interfaces and transceivers that allow the device to communicate with other devices. Device 2100 may also have input device(s) 2114 such as keyboard, mouse, pen, voice input device, touch input device, etc. Output device(s) 2116 such as a display, speakers, printer, etc. may also be included. All these devices are well known in the art and are not discussed at length here.

The example computer systems illustrated in the figures include examples of computer readable storage devices. A computer readable storage device is also a processor readable storage device. Such devices may include volatile and nonvolatile, removable and non-removable memory devices implemented in any method or technology for storage of information such as computer readable instructions, data structures, program modules or other data. Some examples of processor or computer readable storage devices are RAM, ROM, EEPROM, cache, flash memory or other memory technology, CD-ROM, digital versatile disks (DVD) or other optical disk storage, memory sticks or cards, magnetic cassettes, magnetic tape, a media drive, a hard disk, magnetic disk storage or other magnetic storage devices, or any other device which can be used to store the desired information and which can be accessed by a computer Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A see through head mounted display apparatus, comprising:
   a see-through, head mounted display;
   a plurality of sensors cooperating with the display to detect audible and visual behaviors of a subject in a field of view of the apparatus; and
   one or more processing devices in communication with display and the sensors, the one or more processing devices:
   automatically monitor the audible and visual behaviors of the subject by receiving data from the sensors;
   receive supplemental data relating to an emotional state of the subject from a second see-through, head mounted display also monitoring audible and visual behaviors of the subject;
   compute an emotional state of the subject based on the audible and visual behaviors monitored by see-through, head mounted display device and the supplemental data received from the second see-through, head mounted display; and provide feedback to the display indicating computed emotional states of the subject.

2. The apparatus of claim 1 wherein to compute an emotional state, the one or more processing devices:
recognize emitted characteristics of the subject comprising each one of an emitted posture, expression, gesture, audible expression and word from the subject in the input from the sensors and compare the posture, expression, gesture, audible expression and word to a set of emotional states associated with any one or more similar posture, expression, gesture, audible expression and word.

3. The apparatus of claim 2 wherein the one or more processing devices store computed emotional states based on the characteristics relative to recognized audible and visual sensor data for each subject identified.

4. The apparatus of claim 3 wherein the one or more processing devices compute the emotional state of a subject by identifying the subject, retrieving emotional states stored relative to the subject, and comparing recognized audible and visual sensor data to a set of associated emotional states represented by the behaviors exhibited in the behaviors and the computed emotional states stored relative to the subject.

5. The apparatus of claim 1 wherein the one or more processors identify one or more subjects as an unknown subject, determine that no stored emotional state data exists for the unknown subject, and compute emotional states for each unknown subject, and associate the computed emotional states with each unknown subject thereby creating a known subject.

6. The apparatus of claim 1 wherein the one or more processors prompt a wearer of the display for identification of the subjects and are operable to receiving identification of the subjects.

7. The apparatus of claim 1 wherein the one or more processors are operable to determine the emotional state based on scenario information.

8. The apparatus of claim 7 wherein the scenario information is determined by providing the user with a selection of scenarios and receiving a selection of the scenarios.

9. The apparatus of claim 1 further including a communications interface connecting the apparatus to an analysis and feedback service, the interface operable to output sensor data to the service, the interface operable to receive computed emotional states for identified individuals from the service.

10. A computer storage device including instructions operable on a processing device to perform a method comprising the steps of:
receiving input from a plurality of sensors mounted on a see through head mounted display device, the sensors operable to detect audible and visual actions of one or more subjects in a field of view of the see through head mounted display device;
computing an emotional state of the subject based on the audible and visual actions, the computing including determining for each of the one or more subjects whether the one or more subjects is a known subject having historical emotional state data and if so, computing the emotional state based on the historical emotional state data and if not, computing the emotional state data based on unknown subject data, wherein the historical emotional state data comprises emotional state data captured at an earlier time and stored for later use; and
providing feedback to a wearer indicating computed emotional states of the subject.

11. The computer storage device of claim 10 wherein recognizing a behavior comprising any of one of a posture, expression, gesture, audible expression or word in the input from the sensors and comparing posture, expression, gesture, audible expression or word to a set of associated emotional states represented by the behavior to determine a likely emotional state.

12. The computer storage device of claim 10 wherein the instructions further include providing the wearer with a selection of a social scenario, the selection of the social scenario biasing the comparing of the posture, expression, gesture, audible expression or word to associated emotional states.

13. The computer storage device of claim 10 wherein the instructions further include storing computed emotional states indexed to recognized posture, expression, gesture, audible expression or word data for each subject during an interaction.

14. The computer storage device of claim 10 wherein the steps of receiving, continually computing and providing feedback are repeated in sequence in real time.

15. A method for providing emotional state feedback of subjects in a field of view of a see through head mounted display system, comprising:
determining an environment and orientation of the system, the system includes a plurality of sensors and a see-through display;
identifying a crowd of subjects in the field of view;
receiving input from the plurality of sensors mounted on the see through head mounted display device;
recognizing actions of the crowd of subjects comprising any of two or more of a posture, expression, gesture, audible expression and word in the input for the subjects in the crowd of subject from the sensors and comparing recognized actions a set of emotional states determined based on recognized actions performed in combination with each other;
computing an emotional state for the crowd of subjects as a whole based on the recognized actions; and
providing feedback to the wearer indicating emotional state of the crowd of subjects.

16. The method of claim 15 further including determining a social scenario based on the environment, location and orientation of the system and wherein the set of emotional states is determined relative to the social scenario.

17. The method of claim 16 wherein providing feedback includes rendering in the display one of: a specific indication of an emotional state including a visual representation specifying the state, or a positive or negative general indication of a change in emotional state based on tinting the display.

18. The method of claim 17 further including outputting sensor data to an analysis and feedback service and receiving computed emotional states based on the data from the service.

* * * * *